(12) United States Patent
Arumugam et al.

(10) Patent No.: US 6,610,863 B2
(45) Date of Patent: Aug. 26, 2003

(54) CONTINUOUS PROCESS FOR PRODUCING L-ASCORBIC ACID

(75) Inventors: Bhaskar Krishna Arumugam, Kingsport, TN (US); Nick Allen Collins, Fall Branch, TN (US); Transito Lynne Macias, Petal, MS (US); Steven Thomas Perri, Kingsport, TN (US); Jeffrey Earl Grant Powell, Blountville, TN (US); Chester Wayne Sink, Kingsport, TN (US); Michael Roy Cushman, Punta Gorda, FL (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/037,126

(22) Filed: Dec. 21, 2001

(65) Prior Publication Data

US 2002/0151726 A1 Oct. 17, 2002

Related U.S. Application Data

(60) Provisional application No. 60/257,991, filed on Dec. 22, 2000.

(51) Int. Cl.[7] ............................................. C07D 307/62
(52) U.S. Cl. ....................................................... 549/315
(58) Field of Search ......................................... 549/315

(56) References Cited

U.S. PATENT DOCUMENTS

| | | | |
|---|---|---|---|
| 2,265,121 A | | 12/1941 | Reichstein |
| 2,462,251 A | | 2/1949 | Bassford et al. |
| 2,491,065 A | | 12/1949 | Van Eekelen et al. |
| 4,111,958 A | | 9/1978 | Crawford |
| 4,767,870 A | | 8/1988 | Fujiwara et al. |
| 5,128,487 A | | 7/1992 | Tomislav et al. |
| 5,391,770 A | | 2/1995 | Le Fur et al. |
| 5,637,734 A | * | 6/1997 | Honda et al. ................ 549/315 |
| 5,744,618 A | | 4/1998 | Fechtel et al. |
| 5,817,238 A | * | 10/1998 | Makino et al. ................ 21/635 |
| 5,998,634 A | | 12/1999 | Murphy et al. |
| 6,004,445 A | | 12/1999 | Genders et al. |
| 6,197,977 B1 | | 3/2001 | Böttcher et al. |

FOREIGN PATENT DOCUMENTS

| | | | |
|---|---|---|---|
| DE | 3843389 | | 6/1990 |
| DE | 19734086 C1 | | 11/1996 |
| DE | 199 04 821 C1 | | 7/2000 |
| EP | 0554090 A2 | | 4/1983 |
| EP | 1 048 663 A1 | | 11/2000 |
| GB | 428815 | | 5/1935 |
| GB | 1 222 322 | * | 2/1971 |
| GB | 2 034 315 | * | 6/1980 |
| JP | 73015931 | | 5/1973 |
| WO | WO 87/00839 | | 2/1987 |
| WO | WO 97/13761 | | 4/1997 |
| WO | WO 99/07691 | | 2/1999 |
| WO | WO 0046216 | | 8/2000 |

OTHER PUBLICATIONS

Anderson, S. et al., Production of 2–Keto–L–Gulonate, an Intermediate in L–Ascorbate Synthesis, by a Genetically Modified *Erwinia herbicola, Science*, 230, pp. 144–149, 1985.

Regna, P.P. et al.,, Kinetics of Transformation of 2–Ketopolyhydroxy Acids, *J. Am. Chem. Soc.*, 66, pp. 246–250, 1944.

Reichstein, T. et al., Eine ergiebige Synthese der 1–Ascorbinsäure (C–Vitamine)²) *Helv. Chim. Acta*, 17, pp. 311–328, 1934 * See Information Disclosure Statement for Description.

Saito, Y., Direct Fermentation of 2–Keto–L–Gulonic Acid in Recombinant *Gluconobacter oxydans, Biotechnol. Bioeng.*, 58 (2 & 3), pp. 309–315, 1998.

Wankat, *Rate–Controlled Separations*, chapter 10.4, Elsevier Applied Science, p. 524–541, Simulated Moving Bed Fractionation, 1990.

* cited by examiner

*Primary Examiner*—Joseph K. McKane
*Assistant Examiner*—Ebenezer Sackey
(74) *Attorney, Agent, or Firm*—Eric D. Middlemas; Bernard J. Graves, Jr.

(57) ABSTRACT

The present invention provides methods and an apparatus for the manufacture of an L-ascorbic acid product in high yield by direct conversion of an aqueous solution containing 2-keto-L-gulonic acid by contact with an acid catalyst or under thermal self-catalyzed conditions at a conversion level that maximizes the formation of L-ascorbic acid and minimizes decomposition of the L-ascorbic acid thus formed. The separation process for L-ascorbic acid and KLG is operated in such a way that an efficient separation process allows the majority of the KLG to be recycled for further conversion. The product stream from the separation process is then subjected to a recovery step to obtain crystalline L-ascorbic acid product.

36 Claims, 14 Drawing Sheets

SCHEMATIC OF A SIMULATED MOVING BED UNIT

CONTINUOUS PROCESS FOR PRODUCING L-ASCORBIC ACID

This application claims priority to U.S. Provisional Application Serial No. 60/257,991, filed Dec. 22, 2000, the disclosure of which is hereby incorporated herein by reference.

This invention was made with United States Government support under Cooperative Research Agreement No. 70NANB5H1138 awarded by the Advanced Technology Program of the National Institute of Standards and Technology. The United States Government has certain rights in the invention.

FIELD OF THE INVENTION

The present invention relates to a process for producing L-ascorbic acid. More particularly, the present invention relates to a continuous process for producing L-ascorbic acid that minimizes decomposition of the L-ascorbic acid product formed and allows for unreacted starting material to be recycled back into the reaction mix.

BACKGROUND OF THE INVENTION

L-Ascorbic acid (vitamin C) is produced commercially by combined chemical and fermentation processes starting from glucose or sorbose. A common intermediate generated in the commercial process is 2-keto-L-gulonic acid (KLG), or its protected form, diacetone-2-keto-L-gulonic acid. The conversion of 2-keto-L-gulonic acid to L-ascorbic acid may be carried out by esterification with methanol, followed by cyclization using stoichiometric amounts of a base, in a methodology derived from the original Reichstein process (T. Reichstein, A. Grussner, *Helv. Chim. Acta* 17, p. 311–328, 1934). Alternatively, diacetone-2-keto-L-gulonic acid may be cyclized directly, with a loss of acetone followed by consecutive lactonization and enolization, to form ascorbic acid. Direct cyclization of diacetone-2-keto-L-gulonic acid requires extensive purification for recovery of the acetone and other byproducts generated.

Additional modifications to the Reichstein process have focused on removal or simplification of many of the chemical processing steps required for the production of 2-keto-L-gulonic acid. Improvements include controlled esterification of 2-keto-L-gulonic acid and subsequent removal of unesterified starting material (U.S. Pat. No. 5,128,487), as well as improved integration of esterification with subsequent cyclization (U.S. Pat. No. 5,391,770).

Efforts have also been directed to acid catalysis (e.g. U.S. Pat. No. 2,462,251; GB 1,222,322, GB 2,034,315; DE 3843389, WO 99/07691; and WO 00/46216). Acid catalysis employs 2-keto-L-gulonic acid in its acid form, and thus removes the need for the generation of the ester and subsequent steps requiring the addition of stoichiometric base for cyclization with reprotonation of the ascorbate salt to isolate the product in its acid form. As the reprotonation step generates a stoichiometric amount of salt byproduct, acid catalysis can result in significant reduction in waste and processing costs with relatively high yields (>80%) of L-ascorbic acid product. Modifications to improve the process such as the use of organic solvents and surfactants have been described (see e.g. U.S. Pat. No. 5,744,618; WO 98/00839; and JP-B 73015931). Although an improvement over the original Reichstein process, acid catalysis still requires significant handling, recycling, and purfication steps to obtain a high yield of ascorbic acid.

An alternative means of producing ascorbic acid from 2-keto-L-gulonic acid involves an aqueous intramolecular cyclization process without the use of copious amounts of acid catalysts (T. Reichstein, *Helv. Chim. Acta* 17, 1934, pp. 311–328 and BP 428,815). Although aqueous cyclization does not require the extensive purification steps associated with acid catalysis, non-acid catalyzed intramolecular cyclization is associated with relatively low yields. For example, 2-keto-L-gulonic acid may be heated in water saturated with carbon dioxide with 50% yield after fractional crystallization (U.S. Pat. No. 2,265,121). Also, 2-keto-L-gulonic acid or derivatives of 2-keto-L-gulonic acid may be heated to 130–140° C. in water to generate ascorbic acid with yields approximating 50% (U.S. Pat. No. 2,491,065).

Numerous attempts at direct cyclization processes for keto-L-gulonic acid (KLG) and derivatives thereof have been proposed in which the final product is isolated from the cyclization stream by removal of the solvent. Purification of the L-ascorbic acid product is hampered, however, due to the instability of L-ascorbic acid product in aqueous or acid reaction solutions (e.g. P. P. Regna and B. P. Caldwell, *J. Am. Chem. Soc.,* 66, pp. 246–250, 1944), especially when the reaction is operated such that conversion of the 2-keto-L-gulonic acid starting material is nearly complete. Thus, there exists a need for a process that operates at less than complete conversion, but allows for efficient use of the 2-keto-L-gulonic acid starting material and produces purified L-ascorbic acid in high yield. Accordingly, it is to the provision of such processes that the present invention is directed.

SUMMARY OF THE INVENTION

The present invention relates to a process for producing L-ascorbic acid which comprises the steps of subjecting an aqueous solution of 2-keto-L-gulonic acid (KLG) or derivatives of 2-keto-L-gulonic acid to an acid-catalyzed, or self-catalyzed cyclization, followed by separation of the product L-ascorbic acid and any unreacted 2-keto-L-gulonic acid compound so that the unreacted 2-keto-L-gulonic acid starting material may be effectively recycled. The process of the present invention provides methodologies for producing L-ascorbic acid in high yield by optimizing the formation of L-ascorbic acid while operating at a less than complete level of conversion of 2-keto-L-gulonic acid compounds. In this way, the decomposition of L-ascorbic acid product is minimized. The separation step is designed to provide an efficient and non-destructive isolation of unreacted 2-keto-L-gulonic acid starting material so that the 2-keto-L-gulonic acid can be further used for production of more L-ascorbic acid. The L-ascorbic acid isolated during the separation step can then be processed by crystallization or other methods to isolate L-ascorbic acid in its solid form.

In one aspect, the invention comprises a continuous process for manufacturing L-ascorbic acid comprising the steps of:

(a) heating in a reactor an aqueous solution of 2-keto-L-gulonic acid or derivatives of 2-keto-L-gulonic acid to form L-ascorbic acid at a conversion of less than 100 percent;

(b) continuously removing from the reactor a post-reaction solution comprising unreacted 2-keto-L-gulonic acid compound and L-ascorbic acid;

(c) continuously separating L-ascorbic acid from unreacted 2-keto-L-gulonic acid compound in the post-reaction solution to form an L-ascorbic acid rich solution and a solution rich in unreacted 2-keto-L-gulonic acid compound; and (d) continuously recycling the solution rich in 2-keto-L-gulonic acid compound of step (c) back to the reactor.

In another aspect, the present invention comprises an ascorbic acid product made by the methods of the invention.

The present invention also comprises an apparatus for performing the methods of the invention. Thus, in another aspect, the present invention comprises a system for manufacturing L-ascorbic acid comprising:

(a) a reactor for conversion of 2-keto-L-gulonic acid to L-ascorbic acid;

(b) a conduit for the continuous removal of a post-reaction solution comprising unreacted 2-keto-L-gulonic acid and L-ascorbic acid from the reactor prior to complete conversion;

(c) a separation system for continuously separating L-ascorbic acid product from unreacted 2-keto-L-gulonic acid compound in the post-reaction solution to form an L-ascorbic acid rich solution and a 2-keto-L-gulonic acid rich solution;

(d) a conduit for transferring the 2-keto-L-gulonic acid rich solution back to the reactor;

(e) a conduit for transferring fresh 2-keto-L-gulonic acid to the reactor;

(f) a conduit for removing the L-ascorbic acid rich solution for subsequent purification and/or storage;

(g) at least one pump to pump reactants and products through the system; and (h) at least one valve for controlling pressure throughout the system.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

From the foregoing summary, it is apparent that an object of the present invention is provide efficient methods for the production of L-ascorbic acid. These, together with other objects of the present invention, along with various features of novelty which characterize the invention, are pointed out with particularity in the claims.

DETAILED DESCRIPTION OF THE INVENTION

Figure 1:
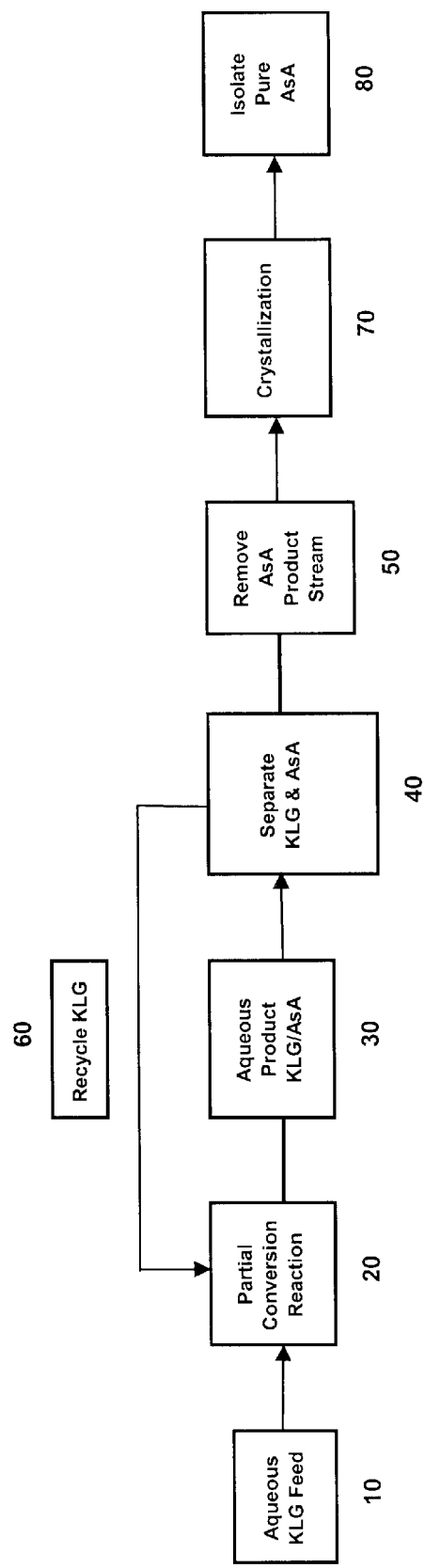
FIG. 1 is a flow diagram illustrating conversion of aqueous (Aq) 2-keto-L-gulonic acid (KLG) to a product comprising a mixture of KLG and ascorbic acid (AsA) with subsequent recycling of the unreacted KLG and crystallization of the AsA product in accordance with an embodiment of the present invention.

The present invention provides methods and systems for the manufacture of L-ascorbic acid in high yield by direct conversion of an aqueous solution containing 2-keto-L-gulonic acid or derivatives of 2-keto-L-gulonic acid at a conversion level that maximizes L-ascorbic acid formation while minimizing L-ascorbic acid decomposition. The L-ascorbic acid product is subsequently separated from any unreacted 2-keto-L-gulonic acid starting material to allow the majority of the unreacted 2-keto-L-gulonic acid starting material to be recycled for further conversion.

In one aspect, the present invention comprises a continuous process for manufacturing L-ascorbic acid comprising the steps of:

(a) heating in a reactor an aqueous solution of 2-keto-L-gulonic acid or derivatives thereof to form L-ascorbic acid at a conversion of less than 100 percent;

(b) continuously removing from the reactor a post-reaction solution comprising unreacted 2-keto-L-gulonic acid compound and L-ascorbic acid product;

(c) continuously separating L-ascorbic acid from unreacted 2-keto-L-gulonic acid compound in the post-reaction solution to form an L-ascorbic acid rich solution and a solution rich in unreacted 2-keto-L-gulonic acid compound; and (d) continuously recycling the solution rich in 2-keto-L-gulonic acid compound of step (c) back to the reactor.

As used herein, the phrase "L-ascorbic acid rich solution" refers to an aqueous solution of L-ascorbic acid in which the ratio of L-ascorbic acid to 2-keto-L-gulonic acid has been increased relative to the post-reaction solution of step (b). Likewise, the phrase "2-keto-L-gulonic acid rich solution" or "solution rich in 2-keto-L-gulonic acid compound" refers to an aqueous solution of 2-keto-L-gulonic acid or derivatives thereof in which the ratio of 2-keto-L-gulonic acid compound to L-ascorbic acid product has been increased relative to the post-reaction solution of step (b). As used herein, derivatives of 2-keto-L-gulonic acid may comprise esters of 2-keto-L-gulonic acid, diacetone-2-keto-L-gulonic acid, and other derivatives of 2-keto-L-gulonic acid which may be cyclized to L-ascorbic acid.

In an embodiment, step (a) is carried out in the absence of an added catalyst. In another embodiment, step (a) is carried out in the presence of a soluble acid catalyst. Preferably, the catalyst is a mineral acid, and even more preferably the mineral acid is selected from the group consisting of HCl, HBr, $H_3PO_4$, and $H_2SO_4$. Alternatively, step (a) may be carried out in the presence of a strongly acid resin catalyst. In a preferred embodiment, the acid resin catalyst may comprise a sulfonated polystyrene cation exchange resin.

The invention employs a partial conversion of 2-keto-L-gulonic acid, or derivatives thereof, of less than 100 percent. Preferably, the conversion of step (a) is about 5 to about 80 percent. More preferably, the conversion of step (a) is 20 to 70 percent. Even more preferably, the conversion of step (a) is 30 to 60 percent.

Generally, the process employs an aqueous solution of 2-keto-L-gulonic acid or derivatives thereof. In an embodiment, the aqueous solution of step (a) comprises 1 to 40 weight percent 2-keto-L-gulonic acid. More preferably, the aqueous solution of step (a) comprises 5 to 30 weight percent 2-keto-L-gulonic acid. Even more preferably, the aqueous solution of step (a) comprises 5 to 15 weight percent 2-keto-L-gulonic acid. In an especially preferred embodiment, the aqueous solution of step (a) is a product stream from a fermentation process for producing 2-keto-L-gulonic acid.

The separation of the 2-keto-L-gulonic acid rich solution from the L-ascorbic acid is preferably highly efficient. In an embodiment, the L-ascorbic acid rich solution of step (c) is comprised of at least 75 weight percent of L-ascorbic acid on a 2-keto-L-gulonic acid and ascorbic acid only basis. Even more preferably, the L-ascorbic acid rich solution of step (c) is comprised of at least 85 weight percent of L-ascorbic acid on a 2-keto-L-gulonic acid and ascorbic acid only basis. And even more preferably, the L-ascorbic acid rich solution of step (c) is comprised of at least 90 weight percent of L-ascorbic acid on a 2-keto-L-gulonic acid and ascorbic acid only basis.

Also, the 2-keto-L-gulonic acid rich solution of step (c) is preferably comprised of at least 75 weight percent of 2-keto-L-gulonic acid compound on a 2-keto-L-gulonic acid and ascorbic acid only basis. Even more preferably, the 2-keto-L-gulonic acid rich solution of step (c) is comprised of at least 85 weight percent of 2-keto-L-gulonic acid compound on a 2-keto-L-gulonic acid and ascorbic acid only basis. Even more preferably, the 2-keto-L-gulonic acid rich solution of step (c) is comprised of at least 90 weight percent of 2-keto-L-gulonic acid compound on a 2-keto-L-gulonic acid and ascorbic acid only basis.

The purities for the separation of the 2-keto-L-gulonic acid compound and the ascorbic acid product are on a 2-keto-L-gulonic acid (KLG) and ascorbic acid (AsA) only basis, and therefore, exclude water as well as non-volatile impurities arising from the KLG feed broth or reactor byproducts. These impurities may account for about 25 to 30 wt % of the total solids in the extract and raffinate products. In a preferred embodiment, the separation of KLG and AsA is so effective that the AsA purity in the extract is nearly identical to the KLG recovery in the raffinate, indicative of the high purity of both fractions.

Even under conditions of partial conversion, the reaction still results in a high yield and high selectivity of L-ascorbic acid product. Thus, in an embodiment, the process step of (a) through (d) provides at least a 50 mole percent yield of L-ascorbic acid. More preferably, the process step of (a) through (d) provides at least a 60 mole percent yield of L-ascorbic acid. Even more preferably, the process step of (a) through (d) provides at least a 65 mole percent yield of L-ascorbic acid.

Generally, the reaction requires elevated temperatures and pressure. Thus, in a preferred embodiment, step (a) is preferably operated at a temperature of about 40° C. to 220° C. Since elevated temperatures are preferred, the reaction is preferably maintained under pressure to maintain an all liquid phase. In an embodiment, therefore, step (a) is operated at a pressure of 1–30 atmospheres.

The process may include additional steps to facilitate operation of the system. For example, in an embodiment, the process further includes after step (b) and before step (c) the step of clarifying the post-reaction solution by adsorption with a polymeric resin or activated carbon material. Alternatively, the process may further include after step (b) and before step (c) the step of concentrating the post-reaction solution by evaporation.

Also, in an embodiment, the process further includes step (e) in which the L-ascorbic acid is purified from the L-ascorbic acid rich solution of (c). Preferably, the L-ascorbic acid is separated from the L-ascorbic acid rich solution by crystallization.

In an embodiment, the separation of step (c) comprises, alternatively, crystallization, chromatography or electrodialysis. In one preferred embodiment, the chromatographic separation of step (c) is conducted by a simulated moving bed process (SMB). Regardless of whether the separation of L-ascorbic acid and 2-keto-L-gulonic acid in step (c) is by SMB or other methods, it is preferred that the weight ratio of 2-keto-L-gulonic acid compound to L-ascorbic acid in the post-reaction solution is from 0.1 to 10, and more preferably, from 0.2 to 5.

In another aspect, the present invention comprises a continuous process for manufacturing L-ascorbic acid comprising the steps of:
(a) heating in a reactor an aqueous solution of 2-keto-L-gulonic acid to form L-ascorbic acid at a conversion of 30 to 60 percent;
(b) continuously removing from the reactor a post-reaction solution comprising unreacted 2-keto-L-gulonic acid and L-ascorbic acid;
(c) continuously separating L-ascorbic acid from unreacted 2-keto-L-gulonic acid in the post-reaction solution utilizing simulated moving bed chromatography, to form an L-ascorbic acid rich solution and a crude 2-keto-L-gulonic acid rich solution, wherein said L-ascorbic acid rich solution is greater than about 90 weight percent L-ascorbic acid on a 2-keto-L-gulonic acid to ascorbic acid (KLG/AsA) basis, and wherein said 2-keto-L-gulonic acid rich solution is greater than about 75 weight percent 2-keto-L-gulonic acid on a KLG/AsA basis; and
(d) continuously recycling the crude 2-keto-L-gulonic acid solution to the reactor.

Step (a) may be carried out in the absence of an added catalyst. Alternatively, step (a) is carried out in the presence of a soluble acid catalyst. The catalyst may be a mineral acid, and even more preferably is selected from the group consisting of HCl, HBr, $H_3PO_4$, and $H_2SO_4$. In another embodiment, step (a) may be carried out in the presence of a strongly acid resin catalyst and even more preferably, a sulfonated polystyrene cation exchange resin.

Generally, the process employs an aqueous solution of 2-keto-L-gulonic acid or derivatives thereof. In an embodiment, the aqueous solution of step (a) comprises 1 to 40 weight percent 2-keto-L-gulonic acid, or more preferably, 5 to 30 weight percent 2-keto-L-gulonic acid, or even more preferably, 5 to 15 weight percent 2-keto-L-gulonic acid. In an especially preferred embodiment, the aqueous solution of step (a) is a product stream from a fermentation process for producing 2-keto-L-gulonic acid.

The separation of the 2-keto-L-gulonic acid rich solution from the L-ascorbic acid is preferably highly efficient. Thus, the 2-keto-L-gulonic acid rich solution of step (c) is preferably comprised of at least 75 weight percent of 2-keto-L-gulonic acid compound on a 2-keto-L-gulonic acid and ascorbic acid only basis, more preferably, at least 85 weight percent of 2-keto-L-gulonic acid compound, and even more preferably, at least 90 weight percent of 2-keto-L-gulonic acid compound.

Even under conditions of partial conversion, the reaction still results in a high yield and high selectivity of L-ascorbic acid product. Thus, steps of (a) through (d) preferably provides at least a 50 mole percent, more preferably, at least a 60 mole percent, and even more preferably, at least a 65 mole percent yield of L-ascorbic acid.

Also, in a preferred embodiment, step (a) is operated at a temperature of about 40° C. to 220° C. and a pressure of 1–30 atmospheres.

The process may include additional steps to facilitate operation of the system. For example, in an embodiment, the process further includes after step (b) and before step (c) the step of clarifying the post-reaction solution by adsorption with a polymeric resin or activated carbon material. Alternatively, the process may further include after step (b) and before step (c) the step of concentrating the post-reaction solution by evaporation.

Also, in an embodiment, the process further includes step (e) in which the L-ascorbic acid is purified from the L-ascorbic acid rich solution of (c). Preferably, the L-ascorbic acid is separated form the L-ascorbic acid rich solution by crystallization.

Referring now to FIG. 1, the present invention relates to a process for producing L-ascorbic acid (AsA) which comprises the steps of subjecting an aqueous solution of 2-keto-L-gulonic acid (KLG) or derivatives of 2-keto-L-gulonic acid 10 to an acid catalyzed cyclization or a thermal self-catalyzed cyclization 20; removing a post-reaction solution comprising unreacted 2-keto-gulonic acid compound and L-ascorbic acid 30; and separating the product L-ascorbic acid and unreacted KLG 40 so that the unreacted KLG may be effectively recycled 60 back to the reactor. Thus, the process provides methodologies for producing L-ascorbic acid in high yield by optimizing the formation of L-ascorbic acid while operating at less than complete conversion of the KLG. By separating the L-ascorbic acid from the reaction prior to complete conversion of KLG, decomposition of the L-ascorbic acid is minimized. The unreacted KLG is separated from the L-ascorbic acid product and recycled back to the reactor to be further used for production of more L-ascorbic acid. The product stream of L-ascorbic acid from the separation step 40 can then be processed by crystallization 70 or other methods to isolate L-ascorbic acid in its solid form 80.

In the present invention, L-ascorbic acid can be readily converted from an aqueous solution of 2-keto-L-gulonic acid, or derivatives thereof, under conditions that achieve partial conversion. The partial conversion allows for a higher production of L-ascorbic acid under these reaction conditions. Preferably, the conversion of 2-keto-L-gulonic acid (KLG) or derivatives thereof to L-ascorbic acid is about 5 to 80 percent, more preferably 20 to 70 percent, and even more preferably, 30 to 60 percent.

While it is preferred that the process be conducted in the absence of a catalyst, "self-catalyzed" as referred to herein, in an alternate embodiment, step (a) is carried out in the presence of a soluble acid catalyst. In an embodiment, the catalyst is a mineral acid. In an embodiment, the catalyst is HCl, HBr, $H_3PO_4$, or $H_2SO_4$.

In yet another embodiment, step (a) is carried out in the presence of a strongly acidic resin catalyst. Preferably, the catalyst is a sulfonated polystyrene cation exchange resin. For example, strongly acidic resin, such as Amberlyst® 15, Amberlyst® 19, Amberlyst® 35 (manufactured by Rohm and Haas Company, Philadelphia, Pa.), Dowex® M-31 or Dowex® G-26 (manufactured by The Dow Chemical Company, Midland, Mich.) may be utilized.

The source of the 2-keto-L-gulonic acid is unimportant in the process of the present invention. Alternative processes, including new fermentation processes for producing 2 keto-L-gluconic acid from glucose (Anderson, S., et al., *Science*, 230, 144–149, 1985) or sorbose (Saito, Y., *Biotechnol. Bioeng.*, 58 (2 & 3), 309–315, 1998) have been, and continue to be, developed. In an embodiment, the step (a) aqueous solution of 2-keto-L-gulonic acid (KLG) is a product stream from a fermentation process for producing KLG. Preferably, an initial purification of this filtrate, such as electrodialysis, ion exchange, or crystallization is undertaken, but is not a precondition for the operation this invention. In the above process, it is preferred that the concentration of 2-keto-L-gulonic acid or a derivative thereof in the aqueous solution of step (a) is about 1 to 40 weight percent, more preferably about 5 to 30 weight percent, and most preferably 5 to 15 weight percent.

The reactions are normally carried out in a solvent. The choice of solvent may be chosen from a wide variety of organic solvents or even water and is only limited by the solubility of the 2-keto-L-gulonic acid and its derivatives and the L-ascorbic acid product in the solvent. Since the 2-keto-L-gulonic acid and its derivatives have limited solubility in non-polar solvents, the preferred solvents would be at least moderately polar. For example, the synthesis of ascorbic acid from 2-keto-L-gulonic acid may utilize an aqueous solvent. As defined herein, "polar" or "moderately polar" comprises molecules which have entities which are positively and/or negatively charged to at least some extent. In an embodiment, the solvent is water. In another embodiment, and especially where esters of 2-keto-L-gulonic are used, the solvent comprises the alcohol corresponding to the alkoxy moiety of the 2-keto-L-gulonic acid ester. Thus, in an embodiment the solvent is methanol. In another embodiment, the solvent is ethanol.

It is anticipated that the post-reaction solution of step (b) may comprise, in addition to 2-keto-L-gulonic acid (or derivatives thereof), additional reaction components such as salt and organic byproducts as well as solvents. For example, in the case of an acid catalyzed conversion, the post-reaction solution may comprise the catalyst. Additionally, the post-reaction solution may comprise dehydrated byproducts such as furylformic acid ($\alpha$-oxo-2-furanacetic acid), 2-furaldehyde, and the like. Other by-products may include higher molecular weight compounds which result from bi-molecular reactions.

Figure 2:
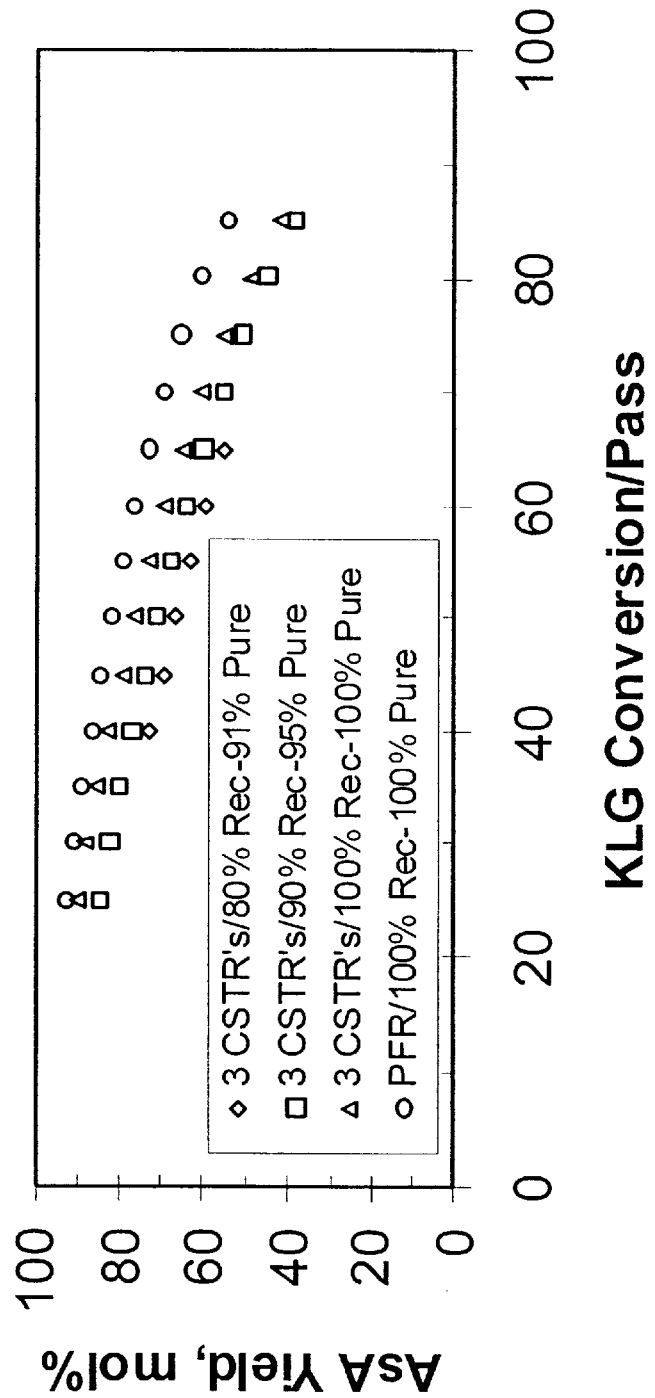
FIG. 2 shows a plot of L-ascorbic acid yield versus single-pass 2-keto-L-gulonic acid (KLG) conversion as simulated for a number of reactor-separator configurations wherein circles (○) indicate plug-flow reactor (PFR) performance with 100% L-ascorbic acid (AsA) recovery and 100% AsA purity in the KLG-AsA separation step; triangles (Δ) indicate performance with a series of three continuous stirred-tank reactors (CSTRs) and perfect KLG-AsA separation efficiency; squares (□) indicate three CSTRs with 90% AsA recovery and 95% AsA purity (on a KLG-AsA only basis) in the separation step; and diamonds (◇) indicate three CSTRs with a poorer separation performance of only 80% AsA recovery and 91% AsA purity.

Conversion of 2-keto-L-gulonic acid substrate and decomposition of L-ascorbic acid product can be described by successive, first-order reactions. Thus, it can be advantageous to perform the conversion of 2-keto-L-gulonic acid substrate in a regime that achieves higher selectivity at lower conversion as opposed to lower selectivity at higher conversion. The reduction in yield which may occur at reduced conversion is preferably negated by efficient separation techniques. For example, as is shown in FIG. 2, the overall yield of L-ascorbic acid is predicted to decrease with increasing conversion per pass with a given set of kinetic parameters for a number of potential reactor-separator schemes. FIG. 2 shows the expected yield for a plug-flow continuous reactor system as well as alternative reactor schemes such as a series of stirred tank batch reactors run in tandem. Also illustrated are the yield penalties associated with less than perfect separation; it can be seen that the overall L-ascorbic acid yields are predicted to dramatically decrease as the L-ascorbic acid recovery and purity in the separator decrease (FIG. 2).

Without being bound to any particular theory, the present invention relies in part on the discovery that partial conversion with efficient recycle dramatically improves the overall yield of L-ascorbic acid. Thus, in an embodiment, an effective separation process, step (c), for separating the components of the aqueous conversion stream comprising the unreacted 2-keto-L-gulonic acid compound (KLG) and L-ascorbic acid is employed to provide for a conversion process with efficient 2-keto-L-gulonic acid compound separation and recycle. The L-ascorbic acid rich solution of step (c) is comprised of at least 75 weight percent of L-ascorbic acid on a KLG and AsA only basis, more preferably at least 85 weight percent, and even more preferably at least 90 weight percent. Further, in step (c), it is preferred that the crude 2-keto-L-gulonic acid rich solution is comprised of at least 75 weight percent of 2-keto-L-gulonic acid compound on a KLG and AsA only basis, more preferably at least 85 weight percent of 2-keto-L-gulonic acid compound, and even more preferably at least 90 weight percent of 2-keto-L-gulonic acid compound. This sequence of unit operations simplifies the overall process and allows higher recovery of the desired L-ascorbic acid product with high purity since the unreacted KLG portion is effectively reused. Furthermore, under self-catalyzing conditions, the present invention obviates the need to separate or remove catalysts and co-solvents prior to recovery of the ascorbic acid product in its crystalline form.

In an embodiment, there may be further provided, after step (b) and before step (c), the step of clarifying the post-reaction solution by adsorption with a polymeric resin such as Dowex® L-285 (Trademark of and manufactured by The Dow Chemical Company, Midland, Michigan) or activated carbon material. For example, such resins may be used to remove high molecular weight colored furfural intermediates formed during the reaction.

Alternatively, or additionally, there may be further provided, after step (b) and before step (c), the step of evaporating the reactor eluant as a means to control volume/mass flow through the system. For example, wherein step (c) comprises crystallization of the L-ascorbic acid, evaporation may be used to increase the relative concentration of L-ascorbic acid prior to crystallization. Alternatively, wherein step (c) comprises chromatographic separation, evaporation reduces the volume of the feed through the system, thereby decreasing the amount of desorbant/eluant required.

Common separation techniques contemplated for separation of 2-keto-L-gulonic acid and L-ascorbic acid through the practice of the invention include fractional crystallization, electrodialysis membrane separation, and chromatographic methods. Fractional crystallization, however, is generally an inefficient means of recovering ascorbic acid directly from a process stream containing a significant amount of 2-keto-L-gulonic acid (KLG) unless combined with other separation techniques (see e.g. U.S. Pat. No. 5,817,238).

Electrodialysis separation operates on the principle that acids with differing pKa's migrate at different rates through a cell containing a membrane so that the more dissociated species will migrate first or preferentially. Electrodialysis membranes operated with anion exchange resins can separate L-ascorbic acid from other components with differing pKa's (see e.g. U.S. Pat. No. 4,767,870, 6,004,445; EP 0 554090 A2). Operating the electrodialysis separation on a stream of 2-keto-L-gulonic acid and L-ascorbic acid would allow the 2-keto-L-gulonic acid to be recycled back to the conversion step and the L-ascorbic acid to be recovered in a subsequent step.

Chromatographic separation may employ, for example, acid retardation based ion exclusion. Ion exclusion separation occurs when acids of different dissociation constants (pKa) are brought in contact with a cation exchange resin. The negative charge on the cation exchange resin repels the negatively charged anions formed by the dissociation of the acids. The stronger acid (i.e. more dissociated) is excluded from the resin structure to a greater extent than a weaker acid. For example, in WO 97/13761, a process is described for recovering L-ascorbic acid by adsorption of L-ascorbic acid on to a resin. The L-ascorbic acid is then desorbed with a neutral solvent such that the concentration of the L-ascorbic acid in the eluant is at least as concentrated as the L-ascorbic acid in the aqueous feed stream.

In an embodiment, the separation process of step (c) comprises SMB chromatography. While other chromatographic methods such as elution chromatography may be employed, simulated moving bed (SMB) chromatography is generally more efficient for a large scale process in that it provides greater separation per volume of adsorbant. For example, U.S. Pat. No. 5,817,238, incorporated herein by reference, describes the use of SMB chromatography for recovery of L-ascorbic acid from a mother liquor obtained during crystallization of L-ascorbic acid. The purified L-ascorbic acid is then recycled back into the crystallization process for further purification. In the separation process described in U.S. Pat. No. 5,817,238, however, the 2-keto-L-gulonic acid concentration is sufficiently dilute (<5% w/v) such that there is no attempt to recover the 2-keto-L-gulonic acid or to recycle it for further production of L-ascorbic acid.

Simulated Moving Bed (SMB) chromatography is a type of liquid chromatography. In the SMB process, the feed, desorbant, and product ports are moved intermittently in the direction of fluid flow. This simulates a counter-current movement of the resin. A detailed description of the SMB process is provided in Wankat (Rate-Controlled Separations, Elsevier Applied Science, 1990, page 524; incorporated herein by reference).

Figure 3:
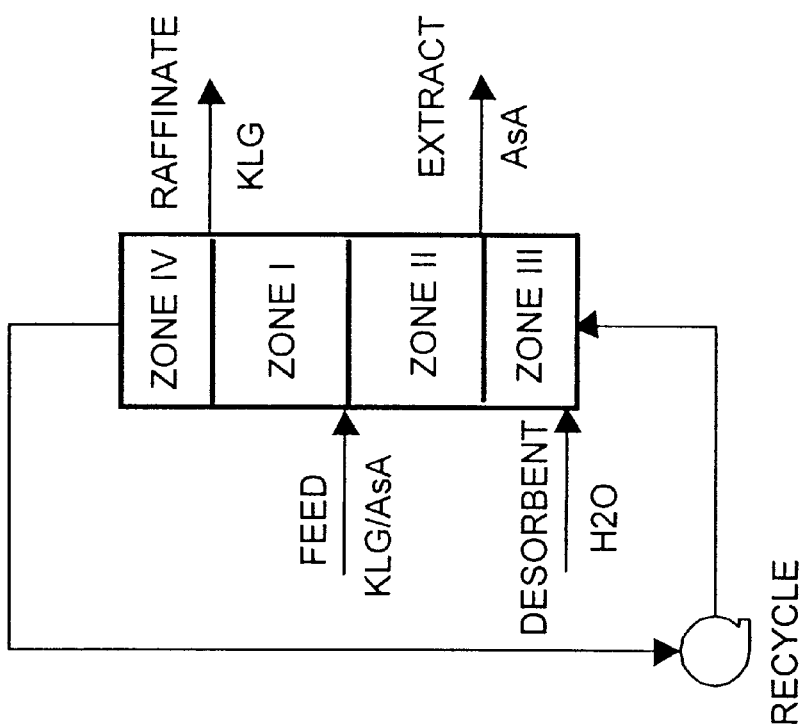
FIG. 3 shows a schematic representation of a typical simulated moving bed (SMB) unit in accordance with an embodiment of the present invention.

For example, and referring now to FIG. 3, a typical SMB unit is comprised of either a single multi-section column or a series of columns with solenoid valves. In both cases, the column or columns are packed with resin and fed both a solution to be separated and a displacer (usually water) via two different ports. Resins suitable for SMB include Dowex Monosphere 99H (The Dow Chemical Co., Midland, Mich.), Amberlite CR1320 H (The Rohm and Haas Co., Philidelphia, Pa.) and Purolite 642 H (Philadelphia, Pa.). Generally, water is used as the desorbant. Other solvents, however, are within the scope of the present invention. The ratio of desorbant:feed (vol/vol) will depend on the parameters of the system. Preferably a desorbant:feed ratio of 6:1 to 1:1 is used. More preferably, the desorbant/feed ratio is about 4:1 to 2:1.

The SMB unit may be operated at room temperature, and is limited at the lower end by the temperature at which the solutions become saturated and at the upper end by the stability of the resin at high temperatures. Thus, suitable temperatures may comprise 20 to 100° C., and more preferably 20 to 70° C.

In SMB, the feed solution's components should separate and exit as at least two product streams (i.e. in this example raffinate, which comprises predominantly KLG, and extract, which is predominantly ascorbic acid). By using an increasing number of distinct zones, the SMB system can be designed to separate multiple components (as for example, other components to be removed from either the recycle or the extract). The ports through which the column is fed and through which the products are extracted move simultaneously and intermittently along the column or along the series of columns to prevent resin exhaustion or saturation and to maintain product purity. Because the column is also fed a displacer (which moves in conjunction with the feed and outlet ports and serves as a regenerant), the product streams will be diluted with the displacer. Typically, the displacer is the same solvent as the feed solvent. The intermittent port movement in the direction of liquid flow simulates the counter-current movement of the resin bed. Thus, as depicted in FIG. 3, the resin is moving faster than the ascorbic acid, but slower than the KLG.

Figure 4:
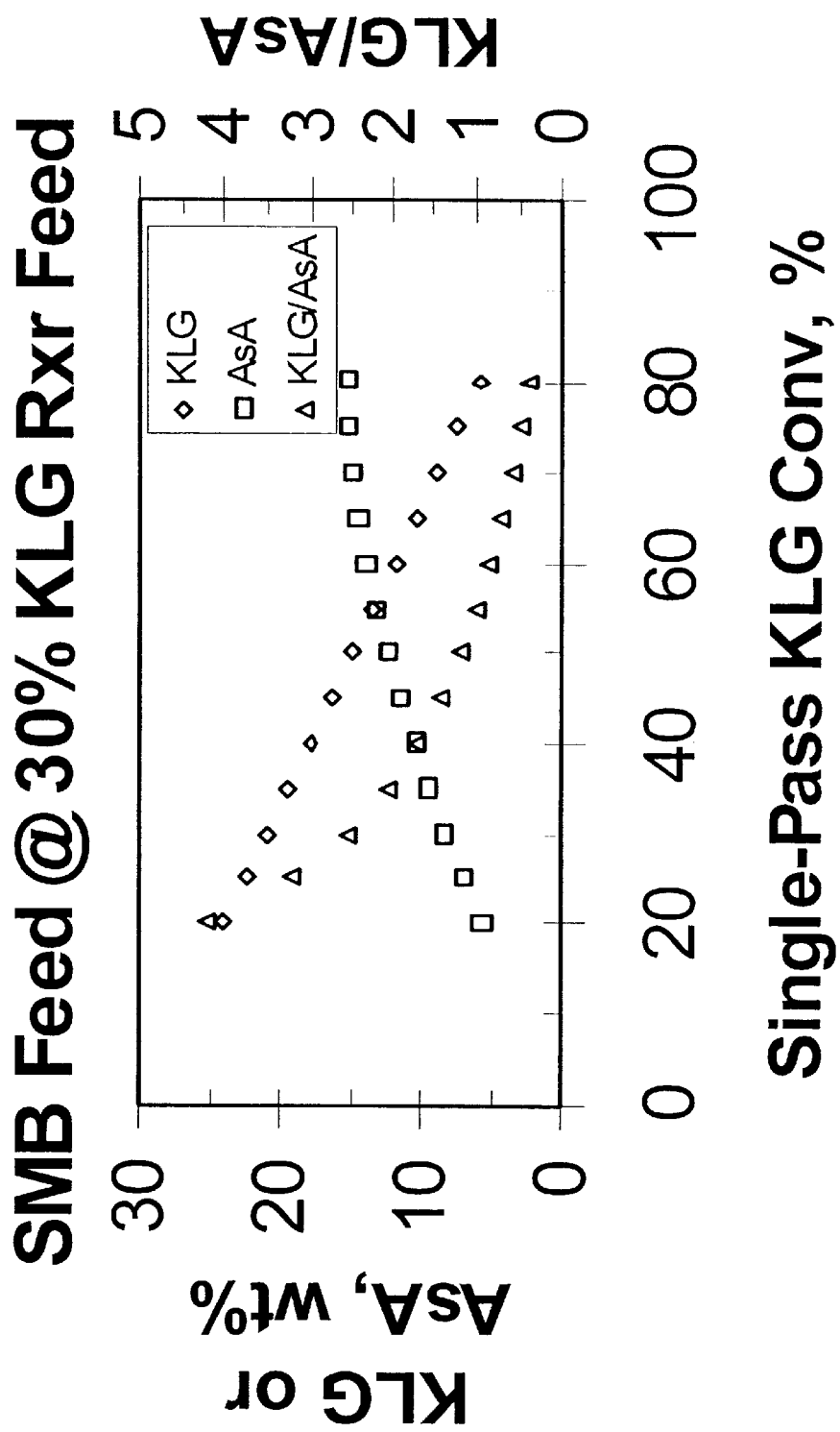
FIG. 4 illustrates an aspect of an embodiment of the present invention showing a plot of the expected composition of a post-reaction solution used for a 2-keto-L-gulonic acid/L-ascorbic acid (KLG/AsA) separation step, e.g., Simulated Moving Bed (SMB) chromatography, at various KLG conversion levels with a 30 wt % KLG feed to the reactor in accordance with an embodiment of the present invention.

For efficient separation of 2-keto-L-gulonic acid and L-ascorbic acid, it is preferred that the ratio of KLG to L-ascorbic acid (on a weight/weight basis) is from 0.1 to 10, more preferably 0.2 to 5 in the post reaction solution. For example, and referring now to FIG. 4, using a feed composition of 30% KLG, a conversion level ranging from 20 to 80% results in a post-reaction solution comprising a ratio of KLG/AsA which ranges from 0.3 to 4, whereas a preferred conversion level of 30 to 60% should result in a post-reaction solution comprising a ratio of KLG/AsA which ranges from 0.8 to 2.5.

In another aspect, the present invention comprises an ascorbic acid product made by the methods of the invention. Thus, the present invention comprises an ascorbic acid product which is made by a continuous process that minimizes decomposition of the L-ascorbic acid formed during the conversion reaction.

Thus in one aspect, the present invention comprises an ascorbic acid product manufactured by a process comprising the steps of:

(a) heating in a reactor an aqueous solution of 2-keto-L-gulonic acid or derivatives of 2-keto-L-gulonic acid to form L-ascorbic acid at a conversion of less than 100 percent;

(b) continuously removing from the reactor a post-reaction solution comprising unreacted 2-keto-L-gulonic acid compound and L-ascorbic acid;

(c) continuously separating L-ascorbic acid from unreacted 2-keto-L-gulonic acid compound in the post-reaction solution to form an L-ascorbic acid rich solution and a solution rich in unreacted 2-keto-L-gulonic acid compound; and (d) continuously recycling the solution rich in 2-keto-L-gulonic compound of step (c) back to the reactor.

In another aspect, the present invention comprises an ascorbic acid product manufactured by a process comprising the steps of:

(a) heating in a reactor an aqueous solution of 2-keto-L-gulonic acid to form L-ascorbic acid at a conversion of 30 to 60 percent;

(b) continuously removing from the reactor a post-reaction solution comprising unreacted 2-keto-L-gulonic acid and L-ascorbic acid;

(c) continuously separating L-ascorbic acid from unreacted 2-keto-L-gulonic acid in the post-reaction solution, utilizing simulated moving bed chromatography to form an L-ascorbic acid rich solution and a crude 2-keto-L-gulonic acid rich solution, wherein said L-ascorbic acid rich solution is greater than about 90 weight percent L-ascorbic acid on a 2-keto-L-gulonic acid and ascorbic acid only basis, and wherein said 2-keto-L-gulonic acid rich solution is greater than about 75 weight percent 2-keto-L-gulonic acid on a 2-keto-L-gulonic acid and ascorbic acid only basis; and d) continuously recycling the crude 2-keto-L-gulonic acid solution to the reactor.

The present invention also comprises an apparatus for performing the methods of the invention. Thus in another aspect, the present invention comprises a system for manufacturing L-ascorbic acid comprising:

(a) a reactor for conversion of 2-keto-L-gulonic acid to L-ascorbic acid;

(b) a conduit for the continuous removal of a post-reaction solution comprising unreacted 2-keto-L-gulonic acid and L-ascorbic acid from the reactor prior to complete conversion;

(c) a separation system for continuously separating L-ascorbic acid product from unreacted 2-keto-L-gulonic acid compound in the post-reaction solution to form an L-ascorbic acid rich solution and a 2-keto-L-gulonic acid rich solution;

(d) a conduit for transferring the 2-keto-L-gulonic acid rich solution back to the reactor;

(e) a conduit for transferring fresh 2-keto-L-gulonic acid to the reactor;

(f) a conduit for removing the L-ascorbic acid rich solution for subsequent purification and/or storage;

(g) at least one pump to pump reactants and products through the system; and (h) at least one valve for controlling pressure throughout the system.

Preferably, the separation system comprises simulated moving bed chromatography. Also preferably, the system of the present invention comprises a unit for clarifying the post-reaction solution by adsorption with a polymeric resin or activated carbon material, wherein said clarifying unit is positioned between the reactor and the separation system. Also preferably, the system of the present invention comprises an evaporator positioned between the reactor and the separation system.

In a preferred embodiment, the system includes means for storing reaction components until they can be transferred to the next unit of the system. For example, in an embodiment, the conduit for transferring fresh 2-keto-L-gulonic acid to the reactor comprises a tank. Also, the system may comprise a tank for storing the reactor product prior to sending the product to the separation system. The system may also comprise tanks for storing the isolated L-ascorbic acid rich solution and the isolated 2-keto-L-gulonic acid rich solution after the SMB separation.

Figure 5:
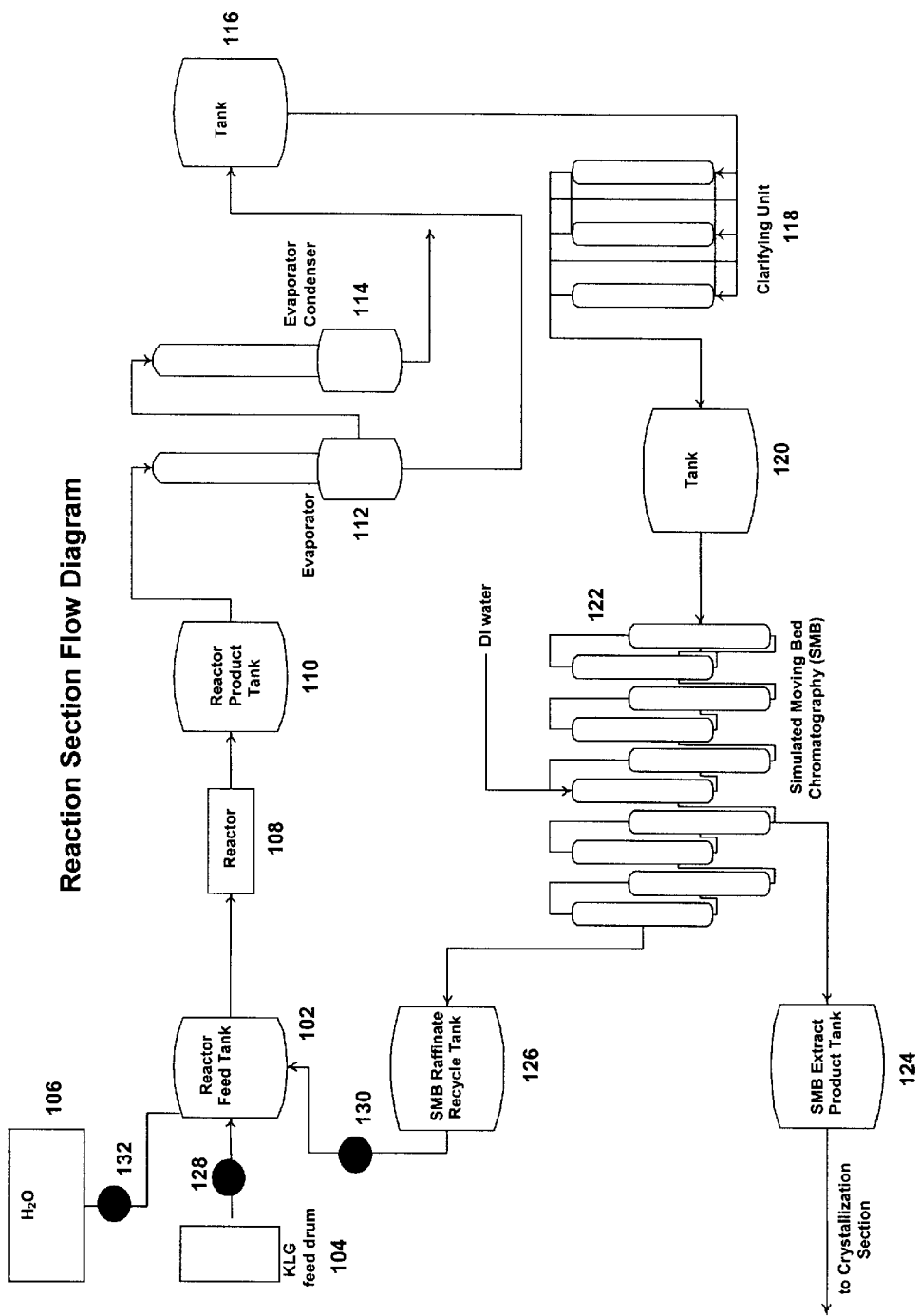
FIG. 5 shows a schematic representation of a reactor used in pilot experiments in accordance with an embodiment of the present invention.

Referring now to FIG. 5, in an embodiment, a system for generation of L-ascorbic acid by partial conversion and recycle of 2-keto-L-gulonic acid (KLG) comprises a continuous reactor 108. Reactor 108 may comprise a tube which is submerged in a silicone oil bath heated to the desired reaction temperature. Feeding into reactor 108 is tank 102 comprising reactor feed. The reactor feed is in turn comprised of fresh KLG (e.g. purified fermentation broth stored in feed drum) or recycled KLG (stored as SMB raffinate recycle) isolated from reactor product.

The system may comprise a simulated moving bed (SMB) chromatographic system 122 for separation of L-ascorbic acid and 2-KLG. In an embodiment, the SMB unit comprises ten columns packed with resin. For example, suitable resins include monodisperse cation exchange resins such as Dowex Monospere 99 H, A-561 (The Dow Chemical Co., Midland, Mich.), Amberlite CR1320 H (The Rohm and Haas Co., Philidelphia, Pa.) and Purolite 642 H (Philadelphia, Pa.). Generally, water is used as the desorbant. Other solvents, however, are within the scope of the present invention. The ratio of desorbant:feed (vol/vol) will depend on the parameters of the system. Preferably a desorbant:feed ratio of 6:1 to 1:1 is used. More preferably, the desorbant/feed ratio is about 4:1 to 2:1, with a ratio of 2.5:1 to 3.5:1 being most preferred.

As described above, the system may comprise tanks for transient storage of starting materials, reaction intermediates, and reaction products. In an embodiment, tank 104 comprises a drum for fresh (i.e. non-recycled) KLG, tank 106 comprises a tank holding water, and tank 126 comprises a tank for KLG recycled from the SMB unit and prior reactions. Movement of fluid into, and out of, the tanks is regulated to have a continuous mass balance throughout the system. For example, pumps 128, 130, and 132 may used to control fluid flow into reactor tank 102, whereas other pumps may be used to control fluid flow throughout other parts of the system.

Generally, components are sized for maximal efficiency in handling the volume of materials cycled through the system. Thus, in an embodiment, the system comprises additional units to improve the control of fluid flow throughout the system. For example, the system may comprise an evaporator system 112, 114, which reduces the volume of material going into the separation system. The system may also include a clarifying system 118 for purification the post-reaction solution prior to SMB separation. Furthermore, the clarification 118 system may comprise tanks 116 and 120 for controlling fluid flow.

In a preferred embodiment, L-ascorbic acid purified by SMB is stored in SMB product tank 124 prior to further purification. Purification of the L-ascorbic acid from the SMB purified product generally comprises crystallization, although other techniques known in the art may be used as well.

Thus, the present invention provides an economical industrial process for efficiently producing L-ascorbic acid from an aqueous solution of 2-keto-L-gulonic acid (KLG) or derivatives thereof. In particular, the process is operated in such a way as to maximize production of L-ascorbic acid in the conversion step while the separation process for L-ascorbic acid and KLG is operated in such a way that an efficient separation process allows the majority of the KLG to be recycled for further conversion. The product stream from the separation process can then be subjected to recovery to obtain crystalline L-ascorbic acid product.

EXAMPLES

Example 1

Figure 6:
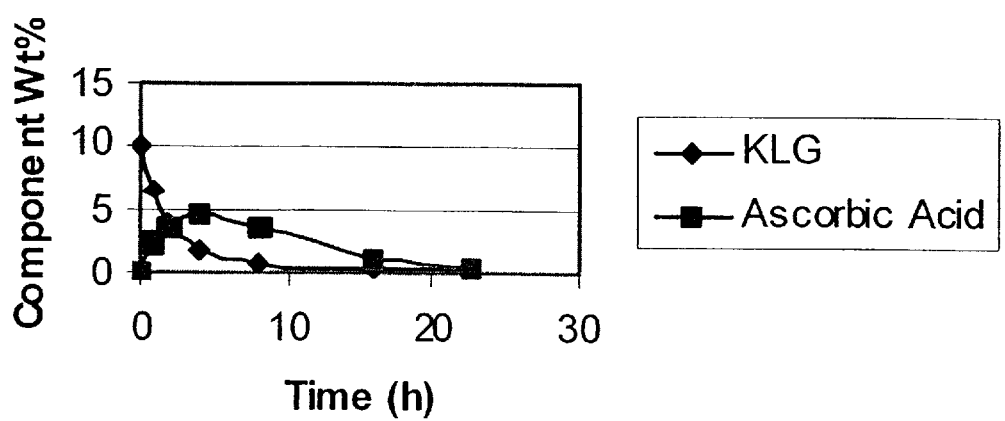
FIG. 6 shows batch conversion of aqueous 2-keto-L-gulonic acid (KLG) with sulfuric acid ($H_2SO_4$) illustrating the maximal yield of L-ascorbic acid (AsA) at partial KLG conversion in accordance with an embodiment of the present invention.

This example demonstrates the batch conversion of an aqueous solution of 2-keto-L-gulonic acid (KLG) exemplifying the high yield of L-ascorbic acid (AsA) at partial conversion with sulfuric acid ($H_2SO_4$) catalysis. A 10 wt % solution of KLG in 2 M $H_2SO_4$ was placed in a sealed vessel and heated to 80° C. The reaction was sampled as a function of time and the composition was analyzed by HPLC. Referring to FIG. 6 as shown in the plot of composition versus time, a maximum concentration of L-ascorbic acid is achieved at about 60% conversion (4 h).

Example 2

Figure 7:
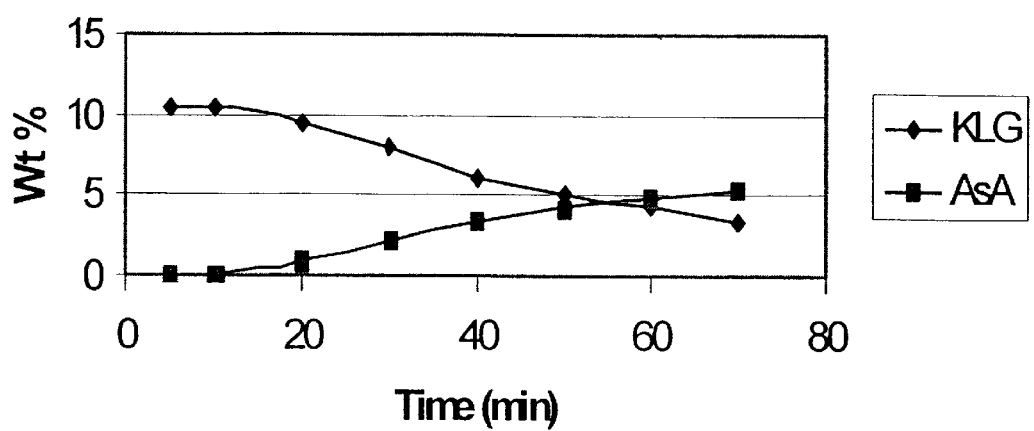
FIG. 7 shows batch conversion of aqueous 2-keto-L-gulonic acid (KLG) with hydrochloric acid (HCl) illustrating the maximal yield of L-ascorbic acid (AsA) at partial KLG conversion in accordance with an embodiment of the present invention.

This example demonstrates the batch conversion of an aqueous solution of 2-keto-L-gulonic acid (KLG) exemplifying the high yield of L-ascorbic acid (AsA) at partial conversion with hydrochloric acid catalysis. A 10% solution of KLG in 3M HCl was placed in a sealed vessel and heated to 90° C. The reaction was sampled as a function of time and the composition was analyzed by HPLC. Referring to FIG. 7 as shown in the plot of composition (wt %) versus time, a concentration of 5.2 wt % L-ascorbic acid is achieved at about 65% conversion (70 min).

Example 3

Figure 8:
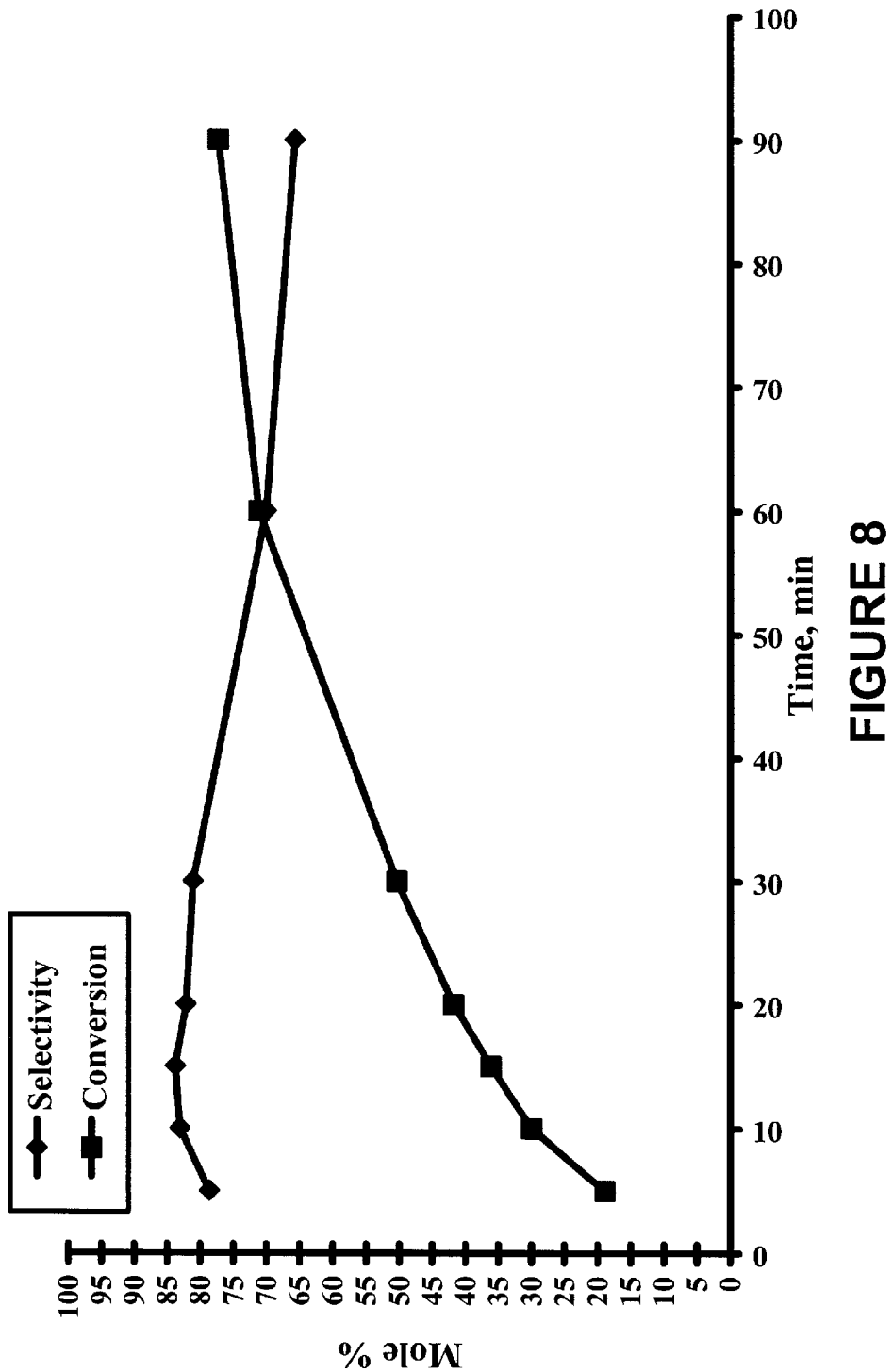
FIG. 8 shows conversion of aqueous 2-keto-L-gulonic acid (KLG) with an acid resin catalyst in a batch reactor exemplifying the change in L-ascorbic acid selectivity over the course of the reaction in accordance with an embodiment of the present invention.

This example demonstrates the batch conversion of an aqueous solution of 2-keto-L-gulonic acid (KLG) exemplifying the change in L-ascorbic acid (AsA) selectivity with time. A batch autoclave was charged with 17 g of water, 15 g of Amberlyst®-15 and heated to 120° C. under 50 psi helium. A total of 49 mL of a solution of 26.4 wt % KLG in water was pumped into the autoclave rapidly to attain approximately a 20 wt % solution of KLG. The reaction was sampled as a function of time and the composition was analyzed by HPLC. Referring to FIG. 8 as shown in the plot of composition (mole %) versus time, a selectivity of 72% L-ascorbic acid is achieved at about 72% conversion.

Example 4

Figure 9:
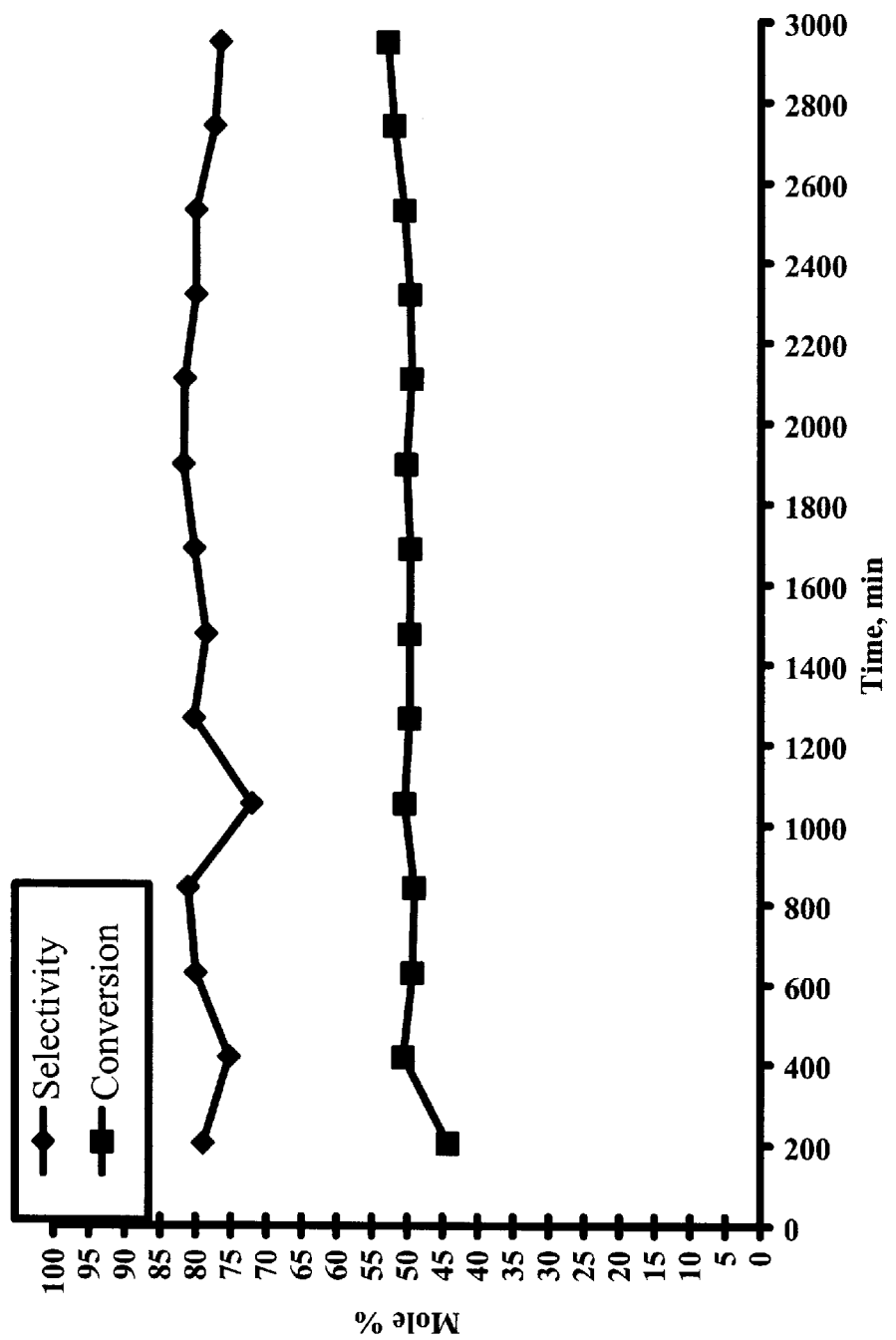
FIG. 9 shows conversion of aqueous 2-keto-L-gulonic acid (KLG) with an acid resin catalyst in a continuous reactor exemplifying the high selectivity of L-ascorbic acid production at partial conversion in accordance with an embodiment of the present invention.

This example demonstrates the continuous conversion of an aqueous solution of crystallized 2-keto-L-gulonic acid (KLG) exemplifying the high selectivity of L-ascorbic acid (AsA) formation at partial conversion with Amberlyst®-15 catalyst. A glass-jacketed column was charged with 350 g of Amberlyst®-15 and heated to 85° C. at atmospheric pressure. An aqueous solution of 10 wt % KLG was pumped in an up-flow direction at a rate of 0.6 mL/min. The effluent containing the product was analyzed by HPLC over the course of 24 h. Referring to FIG. 9, a selectivity of about 80% for L-ascorbic acid is achieved at about 50% conversion.

Example 5

Figure 10:
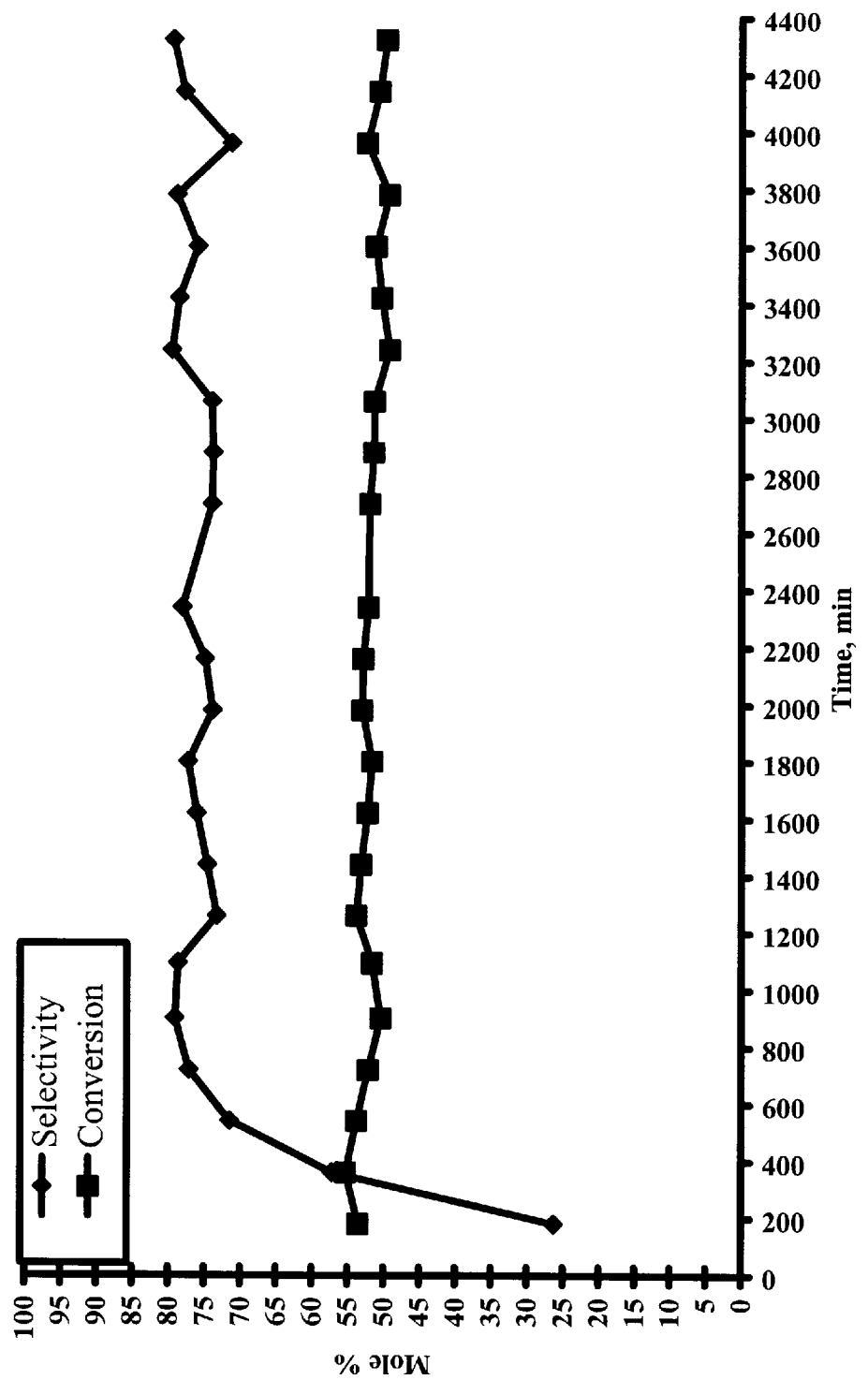
FIG. 10 shows conversion utilizing fermentation broth containing 2-keto-L-gulonic acid (KLG) in a continuous reactor exemplifying selectivity of L-ascorbic acid achieved at partial conversion when using fermentation broth as a feed composition with an acid resin catalyst in accordance with an embodiment of the present invention.

This example demonstrates the continuous conversion of an aqueous fermentation broth containing 2-keto-L-gulonic acid (KLG) exemplifying the use of fermentation broth as a feed composition with high yield of L-ascorbic acid (AsA) at partial conversion with Amberlyst®-15 catalyst. The feed broth was cation exchanged to remove residual cation salts. A glass-jacketed column was charged with 350 g of Amberlyst®-15 and heated to 85° C. at atmospheric pressure. An aqueous fermentation solution of 10.26 wt % KLG was pumped in an up-flow direction at a rate of 0.55 mL/min. The effluent containing the product was analyzed by HPLC over the course of 3 days. Referring to FIG. 10, a selectivity of about 75% for L-ascorbic acid is achieved at about 55% conversion.

Example 6

Figure 11:
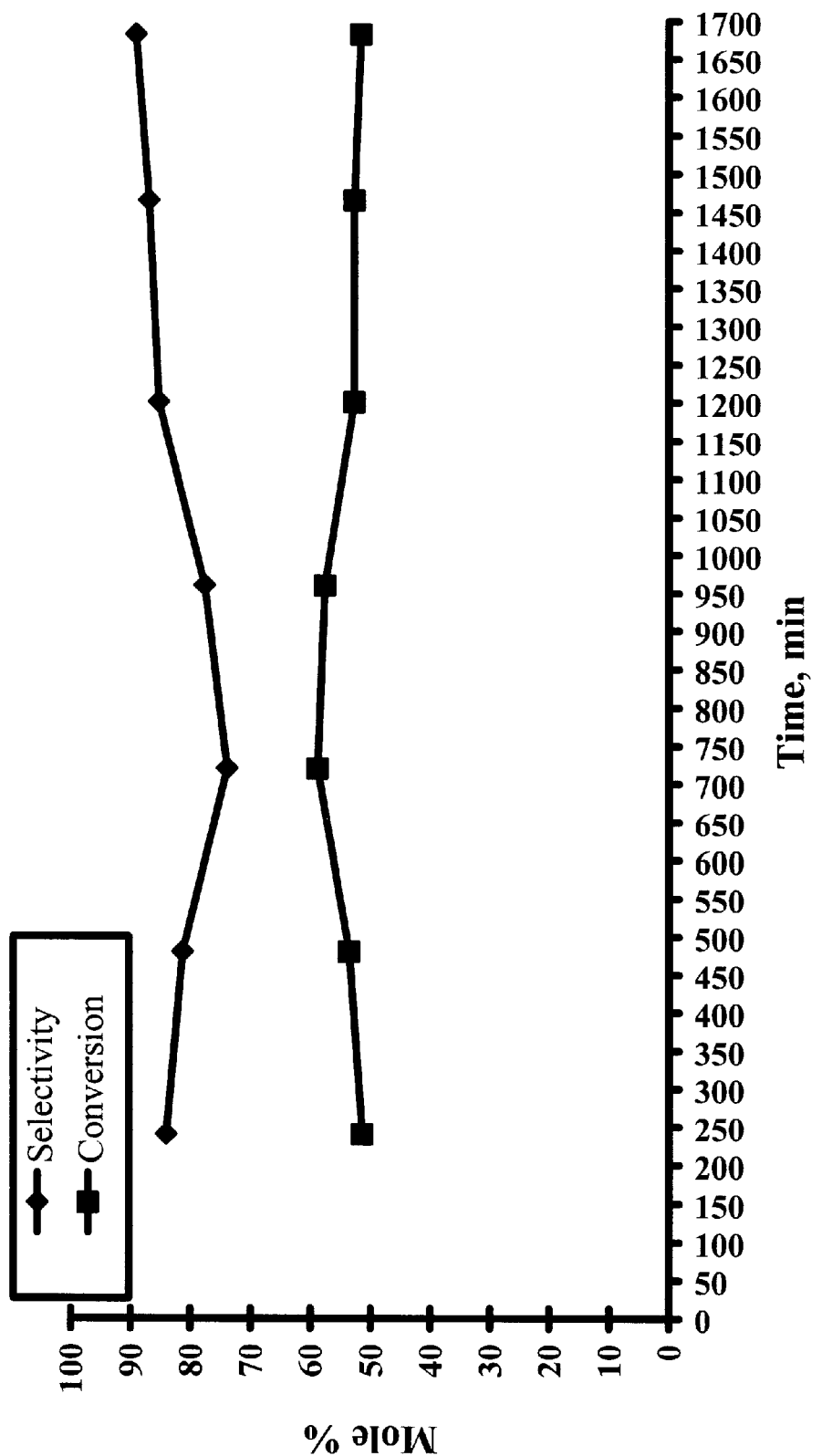
FIG. 11 shows conversion of an aqueous fermentation broth containing 2-keto-L-gulonic acid (KLG) to L-ascorbic acid (AsA) in a continuous reactor exemplifying selectivity achieved at partial conversion when using fermentation broth as a feed composition under self-catalyzing conditions in accordance with an embodiment of the present invention.

This example demonstrates the continuous conversion of an aqueous fermentation broth containing 2-keto-L-gulonic acid (KLG) exemplifying the use of fermentation broth as a feed composition with high yield of L-ascorbic acid (AsA) at partial conversion under self-catalyzing conditions. A 94 foot long, ⅛ inch Teflon® tube with a heated volume of 56.7 mL was immersed in a glycol bath and heated to 125° C. at 40 psi. An aqueous fermentation solution of 11.4 wt % KLG was pumped in at a rate of 1.0 mL/min. The effluent containing the product was analyzed by HPLC over the course of about 1 day. Referring to FIG. 11, a selectivity of about 80% for L-ascorbic acid is achieved at about 55% conversion.

Example 7

This example demonstrates the continuous conversion of an aqueous fermentation broth containing 2-keto-L-gulonic acid (KLG) exemplifying the use of cation and anion exchanged fermentation broth as a feed composition with high yield of L-ascorbic (AsA) acid at partial conversion under self-catalyzing conditions. A 140 foot long, (0.063" ID, 0.125" OD) PFA TEFLON® tube with a heated volume of 86 mL was immersed in an oil bath and heated to 180° C. at 165 psi. An aqueous fermentation solution of 12.8 wt % 2-keto-L-gulonic acid was pumped in at an average rate of 32 mL/min. The reaction was carried out over a period of 190 h and the effluent was analyzed by HPLC. The average conversion and selectivity over the period of operation was 52% conversion and 73% selectivity.

Example 8

This example demonstrates the continuous conversion under self-catalyzing conditions of an aqueous fermentation broth containing 2-keto-L-gulonic acid (KLG) exemplifying the use of a fermentation broth that has been prepared by salt-splitting electrodialysis of the calcium salt. A 140 foot long (0.063" ID, 0.125" OD) PFA TEFLON® tube with a heated volume of 86 mL was immersed in an oil bath and heated to 180° C. at 165 psi. An aqueous fermentation solution of 12.8 wt % 2-keto-L-gulonic acid was pumped in at an average rate of 32 mL/min. The reaction was carried out over a period of 28 h and the effluent was analyzed by HPLC. The average conversion and selectivity over the period of operation was 57% conversion and 72% selectivity.

Example 9

Figure 12:
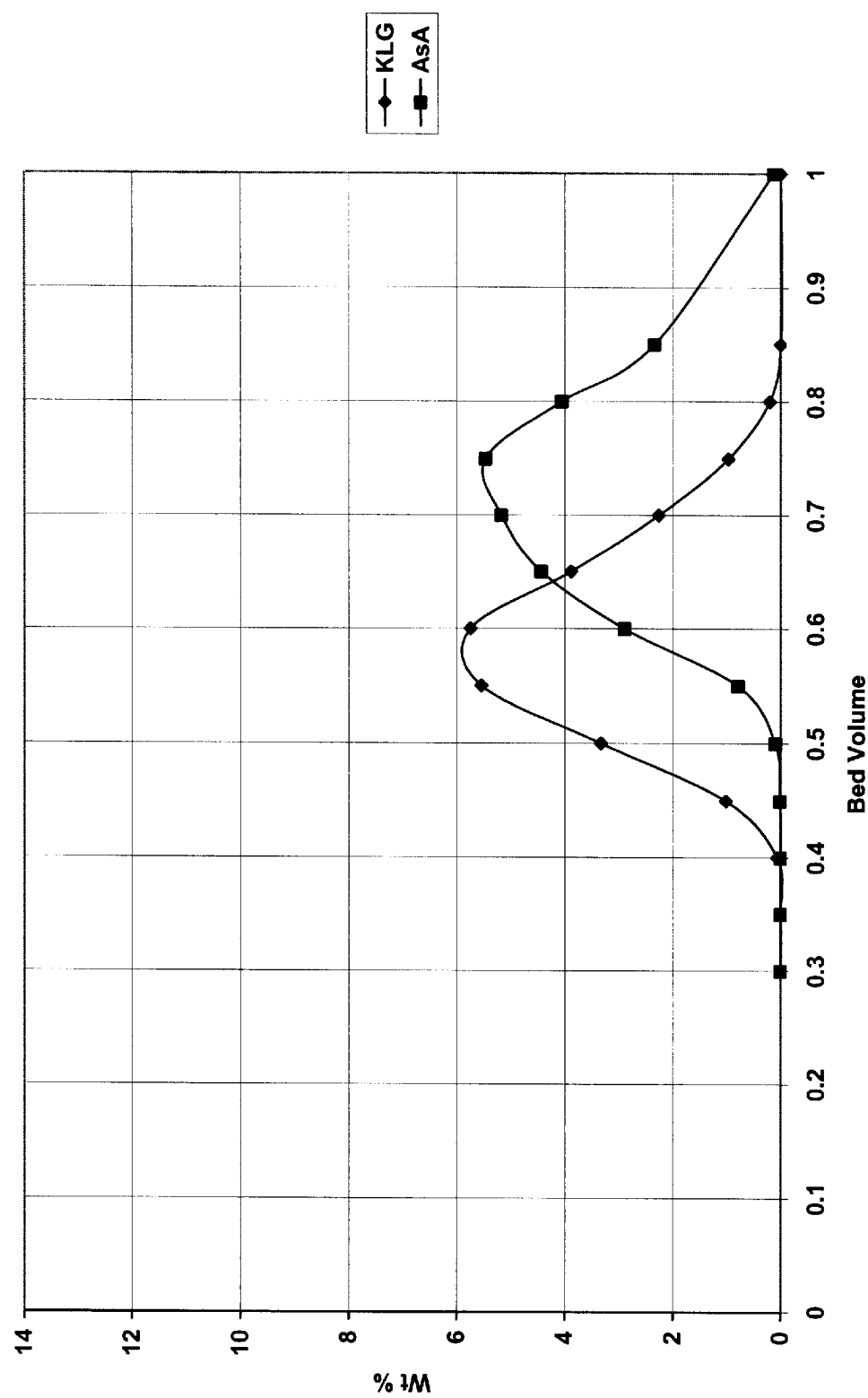
FIG. 12 shows the separation of 2-keto-L-gulonic acid (KLG) and L-ascorbic acid (AsA) by ion exclusion chromatography (0.1 feed pulse/resin bed volume) of a solution containing a 50/50 mixture (15% each) of KLG and L-ascorbic acid in accordance with an embodiment of the present invention.
Figure 13:
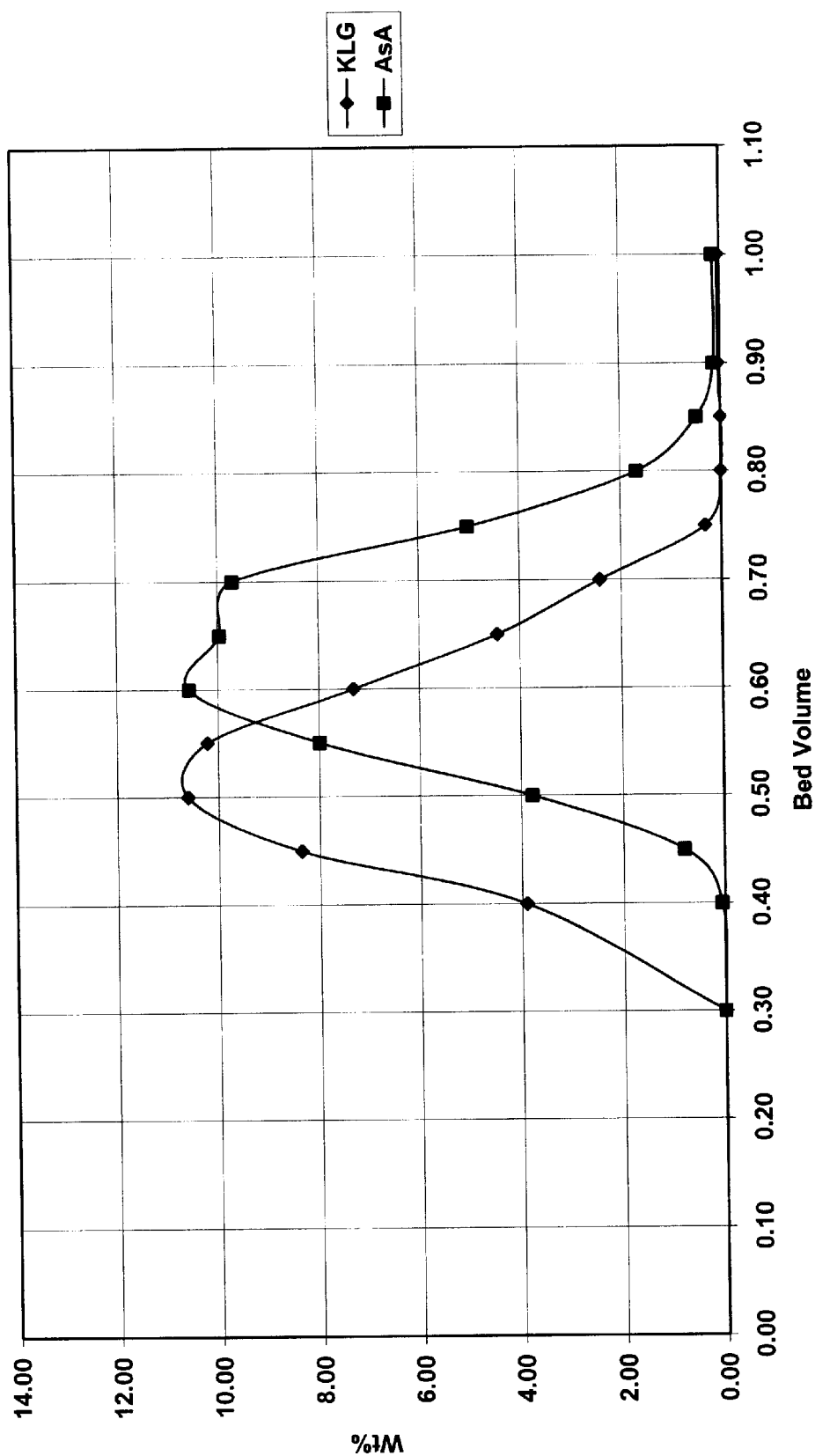
FIG. 13 shows the separation of 2-keto-L-gulonic acid (KLG) and L-ascorbic acid (AsA) by ion exclusion chromatography (0.2 feed pulse/resin bed volume) of a solution containing a 50/50 mixture (15% each) of KLG and L-ascorbic acid in accordance with an embodiment of the present invention.

This example demonstrates the separation of a solution containing a 50/50 mixture of 2-keto-L-gulonic acid (KLG) and L-ascorbic acid (AsA) by ion exclusion. A 0.1 bed volume pulse (FIG. 12) or a 0.2 bed volume pulse (FIG. 13) of a feed mixture consisting of 15% KLG and 15% AsA was fed to a column packed with a Dowex Monosphere 99 H ion exclusion resin. The feed mixture was eluted by water. For both experiments, the peaks of KLG and AsA were separated. These experiments essentially comprises a pulse test showing the feasibility of separating KLG from AsA in a SMB unit.

Example 10

The separation of 2-keto-L-gulonic acid (KLG) from L-ascorbic acid (AsA) was demonstrated on a simulated moving bed (SMB) pilot unit consisting of ten 1.27" ID×30" columns. The columns were packed with Dowex Monosphere 99 H ion exclusion resin in the protonated (H+) form. A feed consisting of 20 wt % KLG and 13.4 wt % L-ascorbic was fed to the SMB unit at a flow rate of 5.0 ml/min. Desorbant (water), raffinate, and extract flow rates were set at 14.2, 10.3, and 8.9 ml/min. After steady state was achieved, the raffinate and extract streams were analyzed. KLG was obtained at 92.4 wt % purity in the raffinate stream and L-ascorbic acid was obtained at 85.5 wt % purity in the extract stream.

Example 11

A second experiment was conducted on the SMB unit described in Example 10. The feed consisted of 18 wt % KLG and 12 wt % L-ascorbic acid. The feed, desorbant, raffinate and extract flow rates were set at 2.8, 14.1, 9.3, and 7.6 ml/min, respectively. After steady state was achieved, the raffinate and extract streams were analyzed. KLG was obtained at 94.4 wt % purity in the raffinate stream and L-ascorbic acid was obtained at 89.9 wt % purity in the extract stream.

Example 12

This example demonstrates the recycle of 2-keto-L-gulonic acid (KLG) material from the simulated moving bed (SMB) (from Example 10, above) mixed with fresh fermentation broth under continuous conversion, self-catalyzing conditions, of an aqueous fermentation broth. A 140 foot long, (0.063" ID, 0.125"OD) PFA TEFLON® tube with a heated volume of 86 mL was immersed in an oil bath and heated to 180° C. at 165 psi. A 12.8 wt % aqueous solution containing equal amounts (based on moles of KLG) of cation and anion exchanged fermentation broth and simulated moving bed effluent containing 2-keto-L-gulonic acid was pumped in at an average rate of 32 mL/min. The reaction was carried out over a period of 20 h and the effluent was analyzed by HPLC. The average conversion and selectivity over the period of operation was 45% conversion and 73% selectivity.

The data for the continuous conversion examples 4–12 is summarized in Table 1 below. Overall, it was found that, under both self-catalyzing and acid catalyzed conditions, and regardless of the feed type (i.e. pure KLG vs. aqueous fermentation broth) or the protonation method employed, high selectivity of L-ascorbic acid resulted under conditions of partial KLG conversion. Additionally, it was found that a blend of fresh KLG and recycled KLG could be used to generate L-ascorbic acid with a selectivity of greater than 70%.

Example 13

This example demonstrates the feasibility of partial conversion of KLG in combination with continuous recycle of KLG purified from the post-reaction solution as a process for the efficient production of L-ascorbic acid. A pilot reactor was developed to test conditions for carrying out the methods of the present invention.

Referring now to FIG. 5, for this experiment, the system included a continuous reactor, a tank comprising reactor feed, and a simulated moving bed (SMB) chromatographic system for separation of L-ascorbic acid and unreacted KLG. The system also included a system for crystallization of L-ascorbic acid in the SMB extract.

Thus, the thermal conversion of 2-keto-L-gulonic acid (KLG) to ascorbic acid (AsA) was performed in 40-feet of coiled ¼-inch OD titanium tubing immersed in a silicone oil (Dow Corning 550) bath. With a wall thickness of 0.035"

TABLE 1

Continuous Conversion Data

| Example | Catalyst | Conversion % | Selectivity % | Feed Type | Protonation Method |
|---------|----------|--------------|---------------|-----------|--------------------|
| 4 | Amberlyst 15 | 50 | 80 | Crystallized 2-Keto-L-gulonic acid | None |
| 5 | Amberlyst 15 | 55 | 75 | Aq. Fermentation Broth | $H_2SO_4$ followed by cation exchange |
| 6 | Self-catalyzing | 55 | 80 | Aq. Fermentation Broth | $H_2SO_4$ |
| 7 | Self-catalyzing | 52 | 73 | Aq. Fermentation Broth | $H_2SO_4$ followed by cation and anion exchange |
| 8 | Self-catalyzing | 57 | 72 | Aq. Fermentation Broth | Salt-splitting electrodialysis of calcium form |
| 9 | Separation Example (Ion Exclusion) | | | | |
| 10 and 11 | Separation Examples (SMB) | | | | |
| 12 | Self-catalyzing | 45 | 73 | Blend of 50% recycled KLG from SMB added to 50% fresh fermentation broth Example 10 | $H_2SO_4$ followed by cation and anion exchange |

$$\% \text{ Conversion} = \frac{\{\text{Initial Feed}[2-KLG] - [2-KLG] \text{ of Product Stream}\}}{\text{Initial Feed}[2-KLG]} \times 100$$

$$\% \text{ Selectivity} = \frac{\{[\text{ascorbic acid}] \text{ of Product Stream} \times (MW\ KLG)\} \times 100}{\{\text{Initial Feed}[2-KLG] - [2-KLG] \text{ of Product Stream}\} \times (MW\ \text{Ascorbic acid})}$$

and heated length of approximately 37 ft, the effective reactor volume was about 185 ml. In these experiments, reactor feed rates ranged from 65 to 75 ml/min with the average of 70 ml/min corresponding to a reactor space-time ranging from 2.47–2.85 min (Table 2). The bath temperature ranged from 177 to 180° C. at the given feed rate. Two heaters were used simultaneously in a 2 ft×2 ft×1 ft (20–25 gals of silicone oil) bath: (1) a 3 kW immersion heater with a variable output set by a powerstat (typically at 50–70%) to provide base load heating and, (2) a 1.2 kW Haake DL30 immersion circulator to control the bath temperature and circulate the oil.

TABLE 2

Reactor Performance

| | Reactor | | | | | SMB Chromatography Performance | | | |
|---|---|---|---|---|---|---|---|---|---|
| Sample | Reactor Temp. °C. | Reactor Feed Rate ml/min | Space Time (min) | KLG Convrsion % | AsA Selectivity mol % | Extract Purity* wt % | Raffinate Purity* wt % | AsA Recovery wt % | KLG Recovery wt % |
| 1 | 177 | 72 | 2.57 | 59.6 | 71.4 | 98.5 | 98.9 | 98.6 | 98.8 |
| 2 | 177 | 72 | 2.57 | 55.0 | 78.1 | 96.2 | 93.8 | 91.5 | 97.3 |

TABLE 2-continued

Reactor Performance

| Sample | Reactor Temp. °C. | Reactor Feed Rate ml/min | Reactor Space Time (min) | KLG Convrsion % | AsA Selectivity mol % | SMB Chromatography Performance ||||
|---|---|---|---|---|---|---|---|---|---|
| | | | | | | Extract Purity* wt % | Raffinate Purity* wt % | AsA Recovery wt % | KLG Recovery wt % |
| 3 | 177 | 72 | 2.57 | 56.3 | 76.8 | 96.5 | 87.5 | 85.3 | 97.1 |
| 4 | 177 | 68 | 2.72 | n.d.** | n.d.** | 97.3 | 89.5 | 89.2 | 97.4 |
| 5 | 177 | 65 | 2.85 | 60.0 | 76.2 | 92.3 | 92.5 | 93.1 | 91.7 |
| 6 | 177 | 75 | 2.47 | 54.4 | 78.0 | 91.0 | 93.4 | 92.6 | 91.9 |
| 7 | 180 | 73 | 2.53 | 58.5 | 76.6 | 97.5 | 96.0 | 96.7 | 96.9 |
| 8 | 180 | 71 | 2.61 | 63.2 | 62.5 | 98.0 | 98.1 | 97.7 | 98.4 |
| 9 | 180 | 69 | 2.68 | 61.1 | 64.9 | 100.0 | 98.6 | 98.7 | 100.0 |
| 10 | 180 | 73 | 2.53 | 60.7 | 71.8 | 100.0 | 98.4 | 98.2 | 100.0 |
| 11 | 180 | 66 | 2.80 | 60.1 | 77.7 | 100.0 | 97.8 | 98.0 | 100.0 |
| 12 | 180 | 66 | 2.80 | 62.1 | 72.4 | 100.0 | 97.5 | 97.8 | 100.0 |
| 13 | 180 | 68 | 2.72 | 61.3 | 72.2 | 100.0 | 97.9 | 98.3 | 100.0 |

*Extract (AsA) and Raffinate (KLG) Purities on a KLG/AsA-only basis
**not determined As shown schematically in FIG. 5, the system included tanks (or other storage means) for transient storage of starting materials, reaction intermediates, and reaction products. For example, feeding into the reactor was a tank comprising reactor feed. The reactor feed was in turn comprised of fresh KLG (e.g. purified fermentation broth stored in feed drum), recycled KLG isolated from the SMB purified reactor product, and deionized water for diluting the reactants to appropriate concentrations. Thus, there were at least three tanks leading into the reactor feed tank: (a) a tank for fresh (i.e. non-recycled) KLG; (b) a second tank for water; and (c) a third tank for KLG recycled from the SMB unit. Movement of fluid into, and out of the tanks was regulated to have a continuous mass balance throughout the system. The system also included an evaporator unit which was used to reduce the volume of material going into the separation system.

Pumps (e.g. FMI Metering Pump; Syosset, N.Y.) were used to pump fluids throughout the system. For example, at least one pump was used to transfer fresh KLG into the pre-reactor tank, one pump was used to transfer the KLG recycle from the SMB system back into the pre-reactor tank, and one pump was used to transfer deionized water to the pre-reactor tank. The pre-reactor tank was 22-liter glass feed tank, and had two sets of dual ISCO syringe pumps to separately feed either aqueous KLG or other components (e.g. catalysts) to the reactor.

To maintain liquid-phase conditions throughout, the pressure in the reactor was kept well above the vapor pressure of water at reaction temperature (about 145 psia at 180° C.) using a Tescom back-pressure regulator. Also, relief valves (250 psig) were included in the system to prevent local over-pressuring in the system. Thus, pressures were bounded by 250-psig relief valves on the KLG feed lines, with a minimum pressure of about 150 psig was imposed to keep the reactor contents in the liquid phase.

The reactor effluent was cooled in a double-pipe (Ti in Cu) exchanger and then filtered (Pall Profile II cartridges, polypropylene, 2.5" OD×5" L, generally 20 μm although some 10 μm cartridges were used) to prevent solid byproducts from going downstream and to protect the back-pressure regulator. Initially a single filter housing (Crall Products) and bypass were used, although multiple (at least two) parallel filters were generally preferred.

All heated sections were constructed of titanium or PFA fluoropolymer. Stainless steel valves, piping, and other components were used both before the reactor and after cooling the effluent. Corrosion coupons were placed in the KLG recycle, KLG feed, and reactor product tanks.

Pilot Reactor Operation

The control strategy for the system as a whole centered around adjusting unit feed (or product in the case of the evaporator) rates to match the unit downstream. Because the SMB feed rate was narrowly constrained, its feed and product rates remained relatively constant. Also, the controlled rates for the evaporator, and SMB were based on concentrated material (>35% solids) while reactor feeds and products were dilute (<15% solids). Thus, the reactor, as the unit furthest away from the SMB feed, required the largest and most frequent rate changes.

The system was designed so that not all the units had to be taken down when one unit failed or required maintenance. Instead, the reactor feed rate was changed to either "catch up" or "slow down" to downstream needs. These feed rate changes required temperature changes as well to maintain target conversion.

The parameters used during a two week run using the system of the present invention are described in Table 2. The oil bath temperature ranged from 177 to 180° C. and the reactor feed rate ranged from 65 to 75 ml/min. Fresh feed from fermentation broth was purified by calcium sulfate precipitation and filtration (Genencor, Palo Alto, Calif.).

It was found that for a conversion level of 2-keto-L-gulonic acid in the range of 50 to 60% (the range of interest), there is a approximately linear relationship between feed rate of the KLG and the temperature required to maintain the appropriate conversion level. Thus, for a feed rate ranging from about 65 to 75 ml/min, a KLG conversion of 60% required temperatures ranging from about 177 to 180° C. (Table 2). At the same feed rate, the temperature needed for 50% conversion was about 5–6° C. lower.

Pilot Reactor Performance

The key measures of reactor performance are KLG conversion and selectivity to AsA. These are calculated simply from reactor feed and product compositions with the following expressions:

$$\text{KLG\_Conversion, \%} = 100\% \times \left(1 - \frac{x_{KLG}^{Product}}{x_{KLG}^{Feed}}\right)$$

$$\text{AsA\_Selectivity, mol \%} = 100\% \times \left(\frac{194.15 \times (x_{AsA}^{Product} - x_{AsA}^{Feed})}{176.13 \times (x_{KLG}^{Feed} - x_{KLG}^{Product})}\right)$$

where $x_i^j$ is the composition by weight of KLG or AsA (i) in the reactor feed or product (j).

Figure 14:
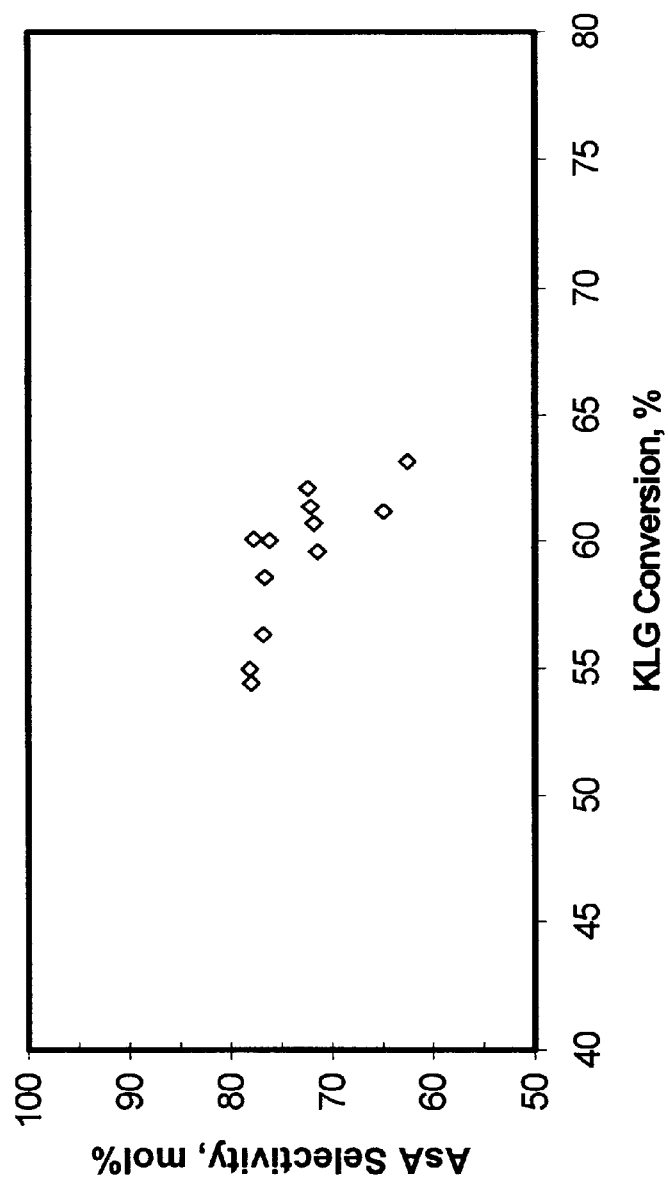
FIG. 14 shows L-ascorbic acid (AsA) selectivity at various 2-keto-L-gulonic acid (KLG) conversion rates for a continuous reactor system using recycled KLG in accordance with an embodiment of the present invention.

In this experiment, samples were taken every 12 hours for analysis. Using the reactor system of the present invention, KLG conversion was generally found to be in the range of about 55–65% (FIG. 14, Table 2). Selectivity of AsA formation ranged from 62.5 to 78.1%, but was greater than 70% for 10 of 12 runs for which selectivity and conversion were determined.

It was found that the SMB chromatography provided a very efficient separation process which was well adapted to the continuous system. Thus, as analyzed by HPLC, the purity of the AsA extract was over 90%, and was found to be essentially completely pure (based on a KLG/AsA only basis) in some samples (Table 2). In addition, the purity of the KLG raffinate was consistently greater than 85%, and greater than 95% for later runs.

Overall, the recovery of AsA from the SMB chromatography separation (on a wt. % basis) was consistently greater than 90% (with only two runs <90%) and generally was found to be greater than 95%. The recovery of KLG was also highly efficient, with most runs approximating 100% recovery.

The purities shown in Table 2 are on a KLG/AsA only basis, and therefore, exclude water as well as non-volatile impurities arising from the KLG feed broth or reactor byproducts. Generally, these impurities accounted for about 25 to 30 wt % of the total solids in the extract and raffinate products. In addition, calculations for recovery were normalized to the amount of KLG and AsA leaving the SMB unit (i.e. on an $KLG_{out}/AsA_{out}$ basis) and therefore, do not account for loss in the SMB unit itself. Still, overall it was found that the separation of KLG and AsA is so effective that the AsA purity in the extract is nearly identical to the KLG recovery in the raffinate.

The invention has been described in detail with particular reference to preferred embodiments thereof, but it will be understood that variations and modifications can be effected within the spirit and scope of the invention. References cited herein are incorporated in their entirety by reference unless otherwise noted.

What is claimed is:

1. A continuous process for manufacturing L-ascorbic acid comprising the steps of:
   (a) heating in a reactor an aqueous solution comprising 2-keto-L-gulonic acid, diacetone-2-keto-L-gulonic acid, or an ester of 2-keto-L-gulonic acid to form L-ascorbic acid at a conversion of less than 100 percent;
   (b) continuously removing from the reactor a post-reaction solution comprising unreacted 2-keto-L-gulonic acid compound and L-ascorbic acid;
   (c) continuously separating L-ascorbic acid from unreacted 2-keto-L-gulonic acid compound in the post-reaction solution to form an L-ascorbic acid rich solution and a solution rich in unreacted 2-keto-L-gulonic acid compound; and
   (d) continuously recycling the solution rich in 2-keto-L-gulonic compound of step (c) back to the reactor.

2. The process according to claim 1 wherein step (a) is carried out in the absence of an added catalyst.

3. The process according to claim 1 wherein step (a) is carried out in the presence of a soluble acid catalyst.

4. The process according to claim 3 wherein the catalyst is a mineral acid.

5. The process according to claim 4 wherein the mineral acid is selected from the group consisting of HCl, HBr, $H_3PO_4$, and $H_2SO_4$.

6. The process according to claim 1 wherein step (a) is carried out in the presence of an acid resin catalyst.

7. The process according to claim 6 wherein the catalyst is a sulfonated polystyrene cation exchange resin.

8. The process according to claim 1 wherein the conversion of step (a) is about 5 to about 80 percent.

9. The process according to claim 1 wherein the conversion of step (a) is 20 to 70 percent.

10. The process according to claim 1, wherein the conversion of step (a) is 30 to 60 percent.

11. The process according to claim 1 wherein the aqueous solution of step (a) comprises 1 to 40 weight percent 2-keto-L-gulonic acid.

12. The process according to claim 1 wherein the aqueous solution of step (a) comprises 5 to 30 weight percent 2-keto-L-gulonic acid.

13. The process according to claim 1 wherein the aqueous solution of step (a) comprises 5 to 15 weight percent 2-keto-L-gulonic acid.

14. The process according to claim 1 wherein the aqueous solution of step (a) is a product stream from a fermentation process for producing 2-keto-L-gulonic acid.

15. The process according to claim 1 wherein on a 2-keto-L-gulonic acid and ascorbic acid only basis, the L-ascorbic acid rich solution of step (c) is comprised of at least 75 weight percent of L-ascorbic acid.

16. The process according to claim 1 wherein on a 2-keto-L-gulonic acid and ascorbic acid only basis, the L-ascorbic acid rich solution of step (c) is comprised of at least 85 weight percent of L-ascorbic acid.

17. The process according to claim 1 wherein on a 2-keto-L-gulonic acid and ascorbic acid only basis, the L-ascorbic acid rich solution of step (c) is comprised of at least 90 weight percent of L-ascorbic acid.

18. The process according to claim 1 wherein on a 2-keto-L-gulonic acid and ascorbic acid only basis, the 2-keto-L-gulonic acid rich solution of step (c) is comprised of at least 75 weight percent of 2-keto-L-gulonic acid compound.

19. The process according to claim 1 wherein on a 2-keto-L-gulonic acid and ascorbic acid only basis, the 2-keto-L-gulonic acid rich solution of step (c) is comprised of at least 85 weight percent of 2-keto-L-gulonic acid compound.

20. The process according to claim 1 wherein on a 2-keto-L-gulonic acid and ascorbic acid only basis, the 2-keto-L-gulonic acid rich solution of step (c) is comprised of at least 90 weight percent of 2-keto-L-gulonic acid compound.

21. The process according to claim 1 wherein the process steps of (a) through (d) provides at least a 50 mole percent yield of L-ascorbic acid.

22. The process according to claim 1, wherein the process steps of (a) through (d) provides at least a 60 mole percent yield of L-ascorbic acid.

23. The process according to claim 1, wherein the process steps of (a) through (d) provides at least a 65 mole percent yield of L-ascorbic acid.

24. The process according to claim 1 wherein step (a) is operated at a pressure of 1–30 atmospheres.

25. The process according to claim 1 wherein step (a) is operated at a temperature of about 40° C. to 220° C.

26. The process according to claim 1 further comprising after step (b) and before step (c) the step of clarifying the post-reaction solution by adsorption with a polymeric resin or activated carbon material.

27. The process according to claim 1 further comprising after step (b) and before step (c) the step of concentrating the post-reaction solution by evaporation.

28. The process according to claim 1 further comprising step (e) in which the L-ascorbic acid is purified from the L-ascorbic acid rich solution.

29. The process according to claim 28 further comprising separating the L-ascorbic acid from the L-ascorbic acid solution by crystallization.

30. The process according to claim 1 wherein the step (c) separation is by crystallization, chromatography or electrodialysis.

31. The process according to claim 30 wherein the chromatography is conducted by a simulated moving bed process.

32. The process according to claim 1 wherein the weight ratio of 2-keto-L-gulonic acid to L-ascorbic acid is from 0.1 to 10 in the post-reaction solution.

33. The process according to claim 31 wherein the weight ratio of 2-keto-L-gulonic acid to L-ascorbic acid is from 0.1 to 10 in the post-reaction solution.

34. The process according to claim 1 wherein the weight ratio of 2-keto-L-gulonic acid to L-ascorbic acid is from 0.2 to 5 in the post-reaction solution.

35. The process according to claim 31 wherein the weight ratio of 2-keto-L-gulonic acid to L-ascorbic acid is from 0.2 to 5 in the post-reaction solution.

36. A process according to claim 1 wherein the aqueous solution of step (a) comprises 2-keto-L-gulonic acid; the conversion of step (a) is from 30 to 60 percent; the step (c) separation is by simulated moving bed chromatography; the L-ascorbic acid rich solution of step (c) is greater than about 90 weight percent L-ascorbic acid on a 2-keto-L-gulonic acid and ascorbic acid only basis; and the 2-keto-L-gulonic acid rich solution of step (c) is greater than about 75 weight percent 2-keto-L-gulonic acid on a 2-keto-L-gulonic acid and ascorbic acid only basis.

* * * * *

UNITED STATES PATENT AND TRADEMARK OFFICE
CERTIFICATE OF CORRECTION

PATENT NO. : 6,610,863 B2
DATED : August 26, 2003
INVENTOR(S) : Perri et al.

It is certified that error appears in the above-identified patent and that said Letters Patent is hereby corrected as shown below:

<u>Title page,</u>
Item [75], "Jeffrey Earl Grant Powell" should be -- Jeffery Earl Grant Powell --

Signed and Sealed this

Twenty-third Day of December, 2003

JAMES E. ROGAN
*Director of the United States Patent and Trademark Office*